United States Patent
Aoshima

(10) Patent No.: US 9,307,943 B2
(45) Date of Patent: Apr. 12, 2016

(54) BIOLOGICAL INFORMATION PROCESSING DEVICE

(75) Inventor: Ichiro Aoshima, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 799 days.

(21) Appl. No.: 13/537,668

(22) Filed: Jun. 29, 2012

(65) Prior Publication Data

US 2013/0006123 A1  Jan. 3, 2013

(30) Foreign Application Priority Data

Jul. 1, 2011 (JP) ................................. 2011-147096
Jul. 6, 2011 (JP) ................................. 2011-149802
Jul. 6, 2011 (JP) ................................. 2011-149804

(51) Int. Cl.
*A61B 5/02* (2006.01)
*A61B 5/00* (2006.01)
*A61B 5/024* (2006.01)
*A61B 5/11* (2006.01)

(52) U.S. Cl.
CPC ............. *A61B 5/681* (2013.01); *A61B 5/02438* (2013.01); *A61B 5/1118* (2013.01)

(58) Field of Classification Search
CPC .. A61B 5/02438; A61B 5/1118; A61B 5/681; A61B 5/024
USPC ................................................. 600/500–509
See application file for complete search history.

(56) References Cited

U.S. PATENT DOCUMENTS

| 5,759,156 A | 6/1998 | Hayakawa et al. |
| 6,099,478 A * | 8/2000 | Aoshima et al. ............... 600/500 |
| 8,649,871 B2 * | 2/2014 | Frei et al. ......................... 607/45 |
| 2009/0024014 A1 | 1/2009 | Sugo et al. |

FOREIGN PATENT DOCUMENTS

| JP | 09-113309 A | 5/1997 |
| JP | 09-154825 A | 6/1997 |
| JP | 10-258040 A | 9/1998 |
| JP | 2004-337408 A | 12/2004 |
| JP | 2009-022484 A | 2/2009 |

* cited by examiner

*Primary Examiner* — Navin Natnithithadha
*Assistant Examiner* — Eric Messersmith
(74) *Attorney, Agent, or Firm* — Global IP Counselors, LLP

(57) ABSTRACT

A method for determining an appropriateness of a calculated pulse rate is provided. In a pulse rate monitor, a pulse rate calculation part calculates the pulse rate of the test subject based on the result detected by a pulse wave sensor. Then, a pulse rate difference calculation part calculates a difference (pulse rate difference) between a reference pulse rate and a calculated pulse rate, and a deviation degree is determined based on the pulse rate difference. Also, a SN ratio calculation part calculates a SN ratio of a pulse wave signal detected by the pulse wave sensor, and a reliability of the calculation result in the pulse rate calculation part is determined based on the SN ratio. Then, a pulse rate appropriateness judgment part determines an appropriateness of the calculated pulse rate based on the pulse rate difference (deviation degree) and the SN ratio (reliability).

10 Claims, 19 Drawing Sheets

| Pulse Range | SN Ratio Threshold Value | Appropriateness Judgment Criteria |
|---|---|---|
| 1ST Pulse Range | - | Every Time |
| 2ND Pulse Range | $\theta 2$ | A Is Satisfied |
| 3RD Pulse Range | $\theta 3$ | (1) A&B Are Satisfied; Or (2) A Is Satisfied And B Is Not Satisfied And D Is Satisfied; Or (3) A Is Satisfied And C Is Not Satisfied & D Is Satisfied |
| 4TH Pulse Range | $\theta 4$ | All A–D Are Satisfied |

$\theta 2 < \theta 3 < \theta 4$

| Condition No. | Condition Item | Contents Of Conditions |
|---|---|---|
| A | Reliability Of Calculation Result Of Pulse Rate (Reliability Condition) | SN Ratio Of Pulse Wave Signal > $\Theta$ |
| B | Possibility Of Body Motion Components (Frequency Condition) | Do Not Exist Cyclic Body Motion Frequency Which Satisfies<br><br>\|Pulse Frequency − Cyclic Body Motion Frequency\| < $\varphi$ |
| C | Consistency Between Body Movement State And Calculated Pulse Rate (Consistency Condition) | C1 Exercise State: Calculated Pulse Rate > HR1<br>C2 Rest State: Calculated Pulse Rate < HR2 |
| D | Reliability Condition Achieved Consecutively | Number Of Times That Condition A Is Consecutively Satisfied In Predetermined Past Time > N |

Fig. 5

| Pulse Range | SN Ratio Threshold Value | Appropriateness Judgment Criteria |
|---|---|---|
| 1st Pulse Range | - | Every Time |
| 2nd Pulse Range | $\Theta 2$ | A Is Satisfied |
| 3rd Pulse Range | $\Theta 3$ | (1) A&B Are Satisfied; Or<br>(2) A Is Satisfied And B Is Not Satisfied And D Is Satisfied; Or<br>(3) A Is Satisfied And C Is Not Satisfied & D Is Satisfied |
| 4th Pulse Range | $\Theta 4$ | All A–D Are Satisfied |

$\Theta 2 < \Theta 3 < \Theta 4$

Fig. 6

| PULSE RANGE | SN RATIO THRESHOLD VALUE | APPROPRIATENESS JUDGMENT CRITERIA |
|---|---|---|
| 1ST PULSE RANGE | $\Theta 1$ | A IS SATISFIED |
| 2ND PULSE RANGE | $\Theta 2$ | (1) A&B ARE SATISFIED; OR<br>(2) A IS SATISFIED AND B IS NOT SATISFIED AND D IS SATISFIED |
| 3RD PULSE RANGE | $\Theta 3$ | (1) A&B&C ARE SATISFIED; OR<br>(2) A&B ARE SATISFIED AND C IS NOT SATISFIED AND D IS SATISFIED; OR<br>(3) A&C ARE SATISFIED AND B IS NOT SATISFIED AND D IS SATISFIED |
| 4TH PULSE RANGE | - | NO JUDGMENT AS APPROPRIATE |

$\Theta 1 < \Theta 2 < \Theta 3$

Fig. 9

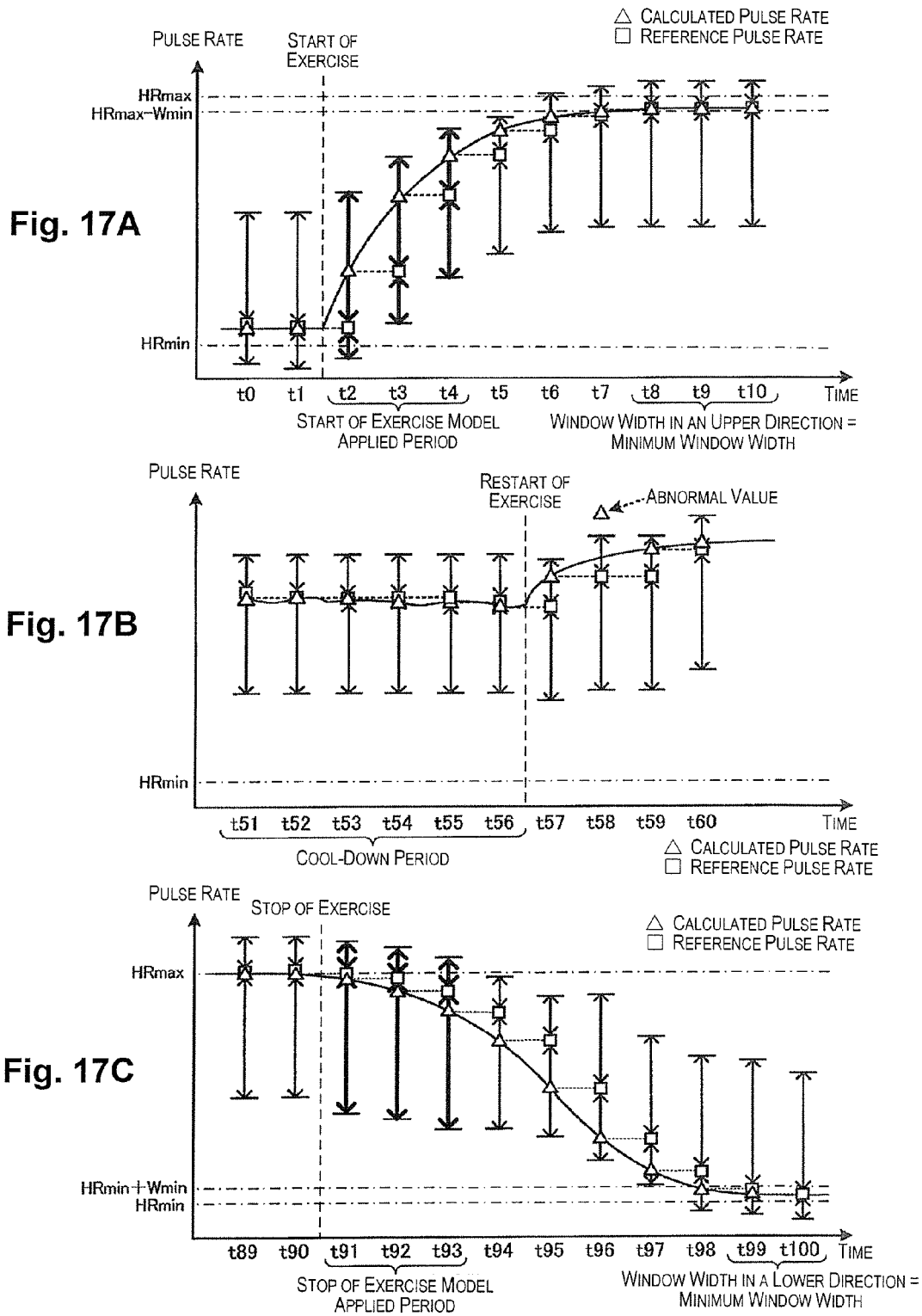

BIOLOGICAL INFORMATION PROCESSING DEVICE

CROSS-REFERENCE TO RELATED APPLICATIONS

This application claims priority to Japanese Patent Application No. 2011-147096 filed on Jul. 1, 2011, Japanese Patent Application No. 2011-149802 filed on Jul. 6, 2011, and Japanese Patent Application No. 2011-149804 filed on Jul. 6, 2011. The entire disclosures of Japanese Patent Application Nos. 2011-147096, 2011-149802 and 2011-149804 are hereby incorporated herein by reference.

BACKGROUND

1. Technical Field

The present invention relates to a biological information processing device.

2. Background Technology

In the art, a pulse rate monitor has been known, as biological information processing devices, to be worn on a part of a test subject's body to manage the exercise and health by measuring the pulse rate of the test subject. The pulse rate monitor detects variations in the blood flow volume in the test subject wearing the device, calculates the pulse rate of the test subject and informs the measurement results of the pulse rate which was calculated (hereafter referred to as "calculated pulse rate"). As a pulse rate monitor, it is known that light is used, ultrasound is used, or cardiograph is used.

In order to correctly measure the pulse rate, it relies heavily on the detection of the variation in the blood flow volume in the test subject with precision. However, a disturbance effect such as changing outside temperature or a physical effect such as shifting the position of the pulse rate monitor device or the position of such device makes low precision to detect the variation in the blood flow volume. Therefore, there has been invented a method for setting a variation acceptable range of the calculated pulse rate and judging an appropriate calculated pulse rate (for example, patent citation 1 and patent citation 2).

Japanese Laid-open Patent Application No. 9-113309 (Patent Document 1) and Japanese Laid-open Patent Application No. 9-154825 (Patent Document 2) are examples of the related art.

SUMMARY

Problems to be Solved by the Invention

A variation acceptable range is used for the method described in the technologies of patent citation 1 or patent citation 2. In this method, however, there is a requirement that an appropriate variation acceptable range has to be set at every calculation event. Specifically, at the time of changing the exercise state of the test subject (start of exercise or stop of exercise etc.), there is a difficulty to have the variation acceptable range follow the change in pulse rate over time because the pulse rate of the test subject changes rapidly.

Also, there are several problems related to how to set a variation acceptable range. For example, even though the calculated pulse rate is correct, the calculated pulse rate is determined as improper when the variation acceptable range is erroneously set. Therefore, patent citation 1 discloses the calculated pulse rate judgement method for determining an appropriate value. The method determines the calculated pulse rate as appropriate when the calculated pulse rate is consecutively off from the variation acceptable range in the same direction (this means that the direction is above the upper limit or the direction falls below the lower limit) for a predetermined number of threshold times (for example, 3 times). However, in the method described above, even if the pulse rate is obviously an abnormal value, it might erroneously judge the pulse rate as appropriate.

To avoid the erroneous judgment, the number of threshold times can be increased. However, if the number of threshold times is increased more than is necessary, it would take a long time to achieve the judgment that the correct calculated pulse rate is appropriate. Therefore, this causes an impaired responsiveness problem (real-time responsiveness).

In addition, the technology of patent citation 2 discloses that for example, the window width having a variation acceptable range (hereafter referred to as "window") is set based on the body motion of the test subject. In detail, when a situation that the body motion of the test subject becomes larger is detected, the window width stretches in an upper direction of the pulse rate (upper direction). In contrast, when a situation that the body motion of the test subject becomes smaller is detected, the window width stretches in a lower direction of the pulse rate (lower direction).

By this method, the window width was set based on only the body motion of the test subject. Therefore, depending on the pulse rate state of the test subject, it does not always realize to achieve the appropriate window setting. For example, there is a situation that the test subject starts exercise from a state being slightly high pulse rate. In detail, there are assumptions that the test subject restarts exercise after cooldown or that the test subject starts walking after running so that the pulse rate goes up the high state.

In the above situations, it does not seem that the pulse rate goes up that much because the pulse rate of the test subject has been already gone up to slightly high. However, when the window width is set based on only the body motion of the test subject, the window width in an upper direction is unnecessarily set wider. In this case, a possibility for detecting an abnormal value in the window increases. On the other hand, in the situation that the test subject stops their movement at the low state of the pulse rate, it causes the same problem as mentioned above because the window width in a lower direction is unnecessarily set wider.

With the above mentioned problems in view, an advantage of the invention is to propose a new method for appropriately judging the calculated pulse rate.

SUMMARY

The 1st embodiment of the invention for solving the above mentioned problems is a biological information processing device including: a pulse rate calculation part for calculating a pulse rate of a test subject; a deviation degree judgment part for judging a deviation degree between a predetermined reference pulse rage and a calculated pulse rate, which was calculated by the pulse rate calculation part; a reliability judgment part for judging a reliability of a calculated result of the pulse rate calculation part; and an appropriateness judgment part for judging an appropriateness of the calculated pulse rate based on the deviation degree and the reliability.

In the 1st embodiment, the deviation degree judgment part determines the deviation degree between the predetermined pulse rate and the calculated pulse rate calculated by the pulse rate calculation part. Also, the reliability judgment part determines the reliability of the calculated pulse rate calculated by the pulse rate calculation part. Then, the appropriateness judgment part determines the appropriateness of the calculated pulse rate based on the deviation degree and the reliability.

The deviation degree is a scale that is an approximate distance between the reference pulse rate and the calculated pulse rate. Normally, it is a rare situation that the pulse rate of the test subject changes rapidly in a short time interval. Thus, the correctness of the calculated pulse rate can be determined from the deviation degree between the reference pulse rate and the calculated pulse rate. In addition, by incorporating with the reliability of the calculation result of the pulse rate calculation part, the appropriateness judgment of the calculated pulse rate is performed absolutely. The reference value is a value as a reference of the pulse rate. For example, a latest calculated pulse rate determined as an appropriate by the appropriateness judgment can be set as a reference pulse rate.

Also, in the 2nd embodiment, in the biological information processing device according to the 1st embodiment, the appropriateness judgment part includes a reliability condition judgment part for judging whether a predetermined reliability condition is satisfied, the predetermined reliability condition easily defines the calculated pulse rate as an appropriate when the deviation degree is smaller, the appropriateness of the calculated pulse rate is judged based on a determination result of the reliability condition judgment part.

In the 2nd embodiment, the reliability condition judgment part determines whether or not the predetermined reliability condition is satisfied. As the deviation degree between the reference pulse rate and the calculated pulse rate becomes smaller, the reliability condition easily defines the calculated pulse rate as an appropriate. Accordingly, it is possible to determine the appropriateness of the calculated pulse rate in accordance with the reliability condition which is made applicable depending on the deviation degree between the reference pulse rate and the calculated pulse rate.

Also, in the 3rd embodiment, in the biological information processing device according to the 2nd embodiment, the appropriateness judgment part judges an appropriateness of the calculated pulse rate based on a number of times affirmative judgment when a predetermined high deviation condition of the deviation degree is satisfied.

As the deviation degree between the reference pulse rate and the calculated pulse rate becomes larger, a possibility for having an erroneous calculated pulse rate increases. Therefore, in the third embodiment, when the deviation degree satisfies the predetermined high deviation degree condition, the appropriateness of the calculated pulse rate is judged based on a number of times affirmative judgment determined by the reliability condition judgment part. When it judges the affirmative judgment continuously, a possibility for having a reliable value of the calculated pulse rate is high. Therefore, the appropriateness of the calculated pulse rate can be determined from the number of times affirmative judgment.

Also, in the 4th embodiment, the biological information processing device according to the 2nd embodiment further includes a body motion detection part for detecting a body motion of the test subject; and a body motion frequency judgment part for judging a frequency of a cyclic body motion of the test subject by using a detection result of the body motion detection part; wherein the appropriateness judgment part includes a frequency condition judgment part for judging whether a predetermined frequency condition is satisfied, the predetermined frequency condition indicates that the frequency of the cyclic body motion of the test subject is away from the frequency of the calculated pulse rate, the appropriateness of the calculated pulse rate is judged by using a determination result of the reliability condition judgment part and a determination result of the frequency condition judgment part when the deviation degree satisfies a predetermined high deviation degree.

In the 4th embodiment, the frequency of the cyclic body motion of the test subject is determined by using the determination result of the body motion detection part. The cyclic body motion means the body motion of the cyclic movement such as swinging the test subject's arms. The predetermined frequency condition defines that the frequency of the cyclic body motion and the frequency of the calculated pulse rate do not approximate to each other. The determination whether or not this condition is satisfied is performed. By this frequency condition, a possibility of acquiring the cyclic body motion as the pulse rate is determined. As described above, as the deviation degree between the reference pulse rate and the calculated pulse rate becomes larger, a possibility having an erroneous calculated pulse rate is high. Thus, when the deviation degree satisfies the predetermined high deviation condition, by performing the appropriateness judgment based on the determination result of the reliability condition judgment part and the determination result of the frequency condition judgment part, the accuracy for the appropriateness judgment of the calculated pulse rate is further improved.

Also, in the 5th embodiment, the biological information processing device according to the 2nd embodiment further includes a body motion detection part for detecting a body motion of the test subject; and a body movement state judgment part for judging a body movement state of the test subject by using a detection result of the body motion detection part; wherein the appropriateness judgment part includes a consistency condition judgment part for judging whether the body movement state and the calculated pulse rate satisfy a predetermined consistency condition, and when the deviation degree satisfies a predetermined high deviation condition, the appropriateness of the calculated pulse rate is judged by using a determination result of the reliability condition judgment part and a determination result of the consistency condition judgment part.

In the 5th embodiment, the body movement state of the test subject is determined by using the determination result of the body motion detection part. The body movement state means the movement state of the test subject's body such as the rest state or the exercise state. The determination whether or not the body movement state and the calculated pulse rate satisfy the predetermined consistency condition is performed. Despite the rest state in the body movement state, the calculated pulse rate indicates a high value unexpectedly, this means that the body movement state and the calculated pulse rate are not consistent (discrepancy). Also, despite the exercise state in the body movement state, the calculated pulse rate indicates a low value unexpectedly, this means that the body movement state and the calculated pulse rate are not consistent. As described above, as the deviation degree between the reference pulse rate and the calculated pulse rate becomes larger, a possibility for having an erroneous calculated pulse rate is high. Accordingly, when the deviation degree satisfies the high deviation condition, by performing the appropriateness judgment based on the determination result of the reliability condition judgment part and the determination result of the consistency condition judgment part, the accuracy for the appropriateness judgment of the calculated pulse rate is further improved.

Also, in the 6th embodiment, in the biological information processing device according to the 5th embodiment, the appropriateness judgment part judges the appropriateness of the calculated pulse rate based on a number of times affirmative judgment being determined by the reliability condition judgment part when a determination result of the reliability condition judgment part is an affirmative judgment and also, a determination result of the consistency condition judgment part is a negative judgment.

In the 6th embodiment, the appropriateness of the calculated pulse rate is determined based on a number of times affirmative judgment determined by the reliability condition judgment part when the determination result of the reliability condition judgment part is an affirmative judgment, and also, the determination result of the consistency condition judgment part is a negative judgment. Even though the reliability of the calculated pulse rate is high, when the body movement state and the calculated pulse rate are not consistent, a possibility for having an erroneous result of the calculated pulse rate is high. Then, in this case, the appropriateness of the calculated pulse rate is determined based on the number of times affirmative judgment by the reliability condition judgment part.

In the 7th embodiment, a biological information processing device includes a pulse rate calculation part for calculating a pulse rate of a test subject; a pulse rate appropriateness judgment part for judging an appropriateness of a calculated pulse rate based on a determination whether the calculated pulse rate calculated by the pulse rate calculation part is within a predetermined variation acceptable range; a variation acceptable width setting part for setting a variation acceptable width as a width of the variation acceptable range based on a value of at least one of a continuance, a frequency, and a number of times that improperness is consecutively judged by the pulse rate appropriateness judgment part.

In the 7th embodiment, the pulse rate of the test subject is calculated by the pulse rate calculation part. The pulse rate appropriateness judgment part judges an appropriateness of a calculated pulse rate based on a determination whether the calculated pulse rate calculated by the pulse rate calculation part is within a predetermined variation acceptable range. When the calculated pulse rate is not within the variation acceptable range, the calculated pulse rate is determined as improper. The variation acceptable width setting part sets a variation acceptable width as a width of the variation acceptable range based on a value of at least one of a continuance, a frequency, and a number of times that improperness is consecutively judged by the pulse rate appropriateness judgment part.

The variation acceptable width is not fixed. The variation acceptable width is flexibly set based on a value of at least one of a continuance, a frequency, and a number of times that improperness is consecutively judged by the pulse rate appropriateness judgment part so that the variation acceptable width can be made applicable. Then, by using the variation acceptable range which includes the set variation acceptable width, it is possible to determine the appropriateness of the calculated pulse rate correctly.

Also, in the 8th embodiment, in the biological information processing device according to the 7th embodiment, the variation acceptable width setting part sets the variation acceptable width by a definition, that is the variation acceptable width increases as the value becomes larger.

In the 8th embodiment, as a value of at least one of a continuance, a frequency, and a number of times that improperness is consecutively judged by the appropriateness judgment of the calculated pulse rate becomes larger, the variation acceptable width increases. Therefore, it is possible the variation acceptable range to follow the changes of the test subject's pulse rate.

In this case, for example, as the 9th embodiment, in the biological information processing device according to the 8th embodiment, the variation acceptable width setting part linearly increases the variation acceptable width for the value.

In the 9th embodiment, the variation acceptable width linearly increases for the value of at least one of a continuance, a frequency, and a number of times that improperness is consecutively judged by the appropriateness judgment of the calculated pulse rate. Even though the pulse rate of the test subject changes rapidly, it is possible to acquire the changing pulse rate with an accuracy and the calculated pulse rate can be determined as an appropriate.

Also, for example, as the 10th embodiment, in the biological information processing device according to the 9th embodiment, as the value becomes larger, the variation acceptable width setting part reduces an increase degree of the variation acceptable width.

In the 10th embodiment, as the value of at least one of a continuance, a frequency, and a number of times that improperness is consecutively judged becomes larger, the increase degree of the variation acceptable width reduces. Therefore, the variation acceptable range being overly stretched is avoided, and a possibility for acquiring an abnormal value can be low. Also, when the pulse rate of the test subject changes rapidly, after that, the change of the pulse rate tends to be slow. Accordingly, it is possible to perform the appropriateness judgment of the calculated pulse rate by setting the variation acceptable range which is suitable for the changing trend of the real human's pulse rate.

Also, in the 11th embodiment, the biological information processing device according to the 7th embodiment further includes a reliability judgment part for judging a reliability of the calculation result of the pulse rate calculation part; wherein the pulse rate appropriateness judgment part determines an appropriateness of the calculated pulse rate by using the variation acceptable range and the reliability.

In the 11th embodiment, the reliability judgment part determines the reliability of the calculation result of the pulse rate calculation part. By using the reliability of the calculation result of the pulse rate in addition to the variation acceptable range, the accuracy of the appropriateness judgment of the calculated pulse rate is improved.

Also, in the 12th embodiment, in the biological information processing device according to the 11th embodiment, the reliability judgment part judges the reliability based on a signal to noise ratio of a signal that detected a pulse wave of the test subject, the pulse rate appropriateness judgment part judges the calculated pulse rate as an appropriate when the signal to noise ratio satisfies a predetermined threshold value condition and also, the calculated pulse rate is within the variation acceptable range.

As the signal to noise ratio of the signal that detected the pulse rate of the test subject is good, a possibility for having the reliability of the calculation result of the pulse rate is high. Then, in the 12th embodiment, the calculated pulse rate is determined as an appropriate when the signal to noise ratio satisfies a predetermined threshold value condition and also, the calculated pulse rate is within the variation acceptable range.

Also, in the 13th embodiment, in the biological information processing device according to the 7th embodiment, the variation acceptable range is a range defined as a predetermined reference pulse rate, and the biological information processing device according to the 7th embodiment further includes a reference pulse rate update part for updating the reference pulse rate by the calculated pulse rate when the calculated pulse rate is determined as an appropriate.

In the 13th embodiment, when the pulse rate appropriateness judgment part determines the calculated pulse rate as an appropriate, the reference pulse rate update part updates a reference pulse rate as a reference of the variation acceptable range in the calculated pulse rate. As a result, the reference of the variation acceptable range is made applicable, so that it is possible to perform the appropriateness judgment of the calculated pulse rate by setting an appropriate variation acceptable range in each case.

In the 14th embodiment, a biological information processing device includes a pulse rate calculation part for calculating a pulse rate of a test subject; a pulse rate appropriateness judgment part for judging an appropriateness of a calculated pulse rate based on a determination whether the calculated pulse rate calculated by the pulse rate calculation part is within a predetermined variation acceptable range; a variation acceptable width setting part for setting a variation acceptable width as a width of the variation acceptable range based on a predetermined reference pulse rate.

In the 14th embodiment, the pulse rate calculation part calculates the pulse rate of the test subject. Then, the pulse rate appropriateness judgment part judges an appropriateness of a calculated pulse rate based on the determination whether the calculated pulse rate calculated by the pulse rate calculation part is within the predetermined variation acceptable range. In this case, the variation acceptable width setting part sets a variation acceptable width as a width of the variation acceptable range based on a predetermined reference pulse rate.

The reference pulse rate is a pulse rate for the reference of the variation acceptable range. For example, the reference pulse rate can be set as the latest pulse rate which is determined as an appropriate by the appropriateness judgment. Then, by using the variation acceptable range which includes the set variation acceptable width, it is possible to determine the appropriateness of the calculated pulse rate correctly.

Also, in the 15th embodiment, the biological information processing device according to the 14th embodiment, as the reference pulse rate becomes lower, the variation acceptable width setting part increases a variation acceptable width in an upper direction relative to the reference pulse rate as a reference.

In the 15th embodiment, as the reference pulse rate becomes lower, the variation acceptable width in an upper direction relative to the reference pulse rate as a reference increases. In a state that the pulse rate is low, the pulse rate becomes difficult to go down, and it tends to go up. Accordingly, as the reference pulse rate becomes lower, the variation acceptable width in an upper direction increases so that it is possible to set the variation acceptable range which is suitable for the trend of the human's pulse rate.

Also, as the 16th embodiment, in the biological information processing device according to the 14th embodiment, as the reference pulse rate becomes higher, the variation acceptable width setting part increases a variation acceptable width in a lower direction relative to the reference pulse rate as a reference.

In the 16th embodiment, as the reference pulse rate becomes higher, the variation acceptable width in a lower direction relative to the reference pulse rate as a reference increases. In a state that the pulse rate is high, the pulse rate becomes difficult to go up, and it tends to go down. Accordingly, as the reference pulse rate becomes higher, the variation acceptable width in an lower direction increases so that it is possible to set the variation acceptable range which is suitable for the trend of the human's pulse rate.

Also, as the 17th embodiment, in the biological information processing device according to the 14th embodiment, as the reference pulse rate becomes lower, the variation acceptable width setting part increases a variation acceptable width in an upper direction relative to the reference pulse rate as a reference, and also, as the reference pulse rate becomes higher, the variation acceptable width setting part increases a variation acceptable width in a lower direction relative to the reference pulse rate as a reference, an increase degree of the variation acceptable width in an upper direction increases in comparison with an increase degree of the variation acceptable width in a lower direction.

In the 17th embodiment, as the reference pulse rate is lower, the variation acceptable width in an upper direction relative to the reference pulse rate as a reference increases, and also, as the reference pulse rate becomes higher, the variation acceptable width in a lower direction relative to the reference pulse rate as a reference increases. In this case, the increase value of the variation acceptable width in an upper direction increases in comparison with the increase value of the variation acceptable width in a lower direction. When the pulse rate goes up, the variation tends to be larger in comparison with the case that the pulse rate goes down. In a simple term, the pulse rate has a tendency to go up, rather than to go down. Then, an increase degree of the variation acceptable width in an upper direction increases in comparison with an increase degree of the variation acceptable width in a lower direction so that it is possible to set the variation acceptable width considered with the feature of the human's pulse rate.

Also, in the 18th embodiment, the biological information processing device according to the 15th embodiment further includes an exercise state judgment part for judging an exercise state of the test subject; wherein the variation acceptable width setting part increases an increase degree of the variation acceptable width in an upper direction at a start of exercise as a determination result of the exercise state in comparison with an increase degree of the variation acceptable width in an upper direction at a steady time.

In the 18th embodiment, an increase degree of the variation acceptable width in an upper direction at the start of exercise as a determination result of the exercise state increases in comparison with an increase degree of the variation acceptable width in an upper direction at the steady time. When a human starts exercise, the pulse rate tends to go up rapidly. Then, the variation acceptable width in an upper direction at the start of exercise stretches in comparison with at the steady time so that it is possible the variation acceptable range to follow the rapid raise of the pulse rate.

Also, in the 19th embodiment, the biological information processing device according to the 16th embodiment further includes an exercise state judgment part for judging an exercise state of the test subject; wherein the variation acceptable width setting part increases an increase degree of the variation acceptable width in a lower direction at a stop of exercise as a determination result of the exercise state in comparison with an increase degree of the variation acceptable width in a lower direction at a steady time.

In the 19th embodiment, the increase degree of the variation acceptable width in a lower direction at the stop of exercise as a determination result of the exercise state increases in comparison with the increase degree of the variation acceptable width in a lower direction at the steady time. When a human stops exercise, the pulse rate tends to go down rapidly. Then, the variation acceptable width in a lower direction at the stop of exercise stretches in comparison with at the steady time so that it is possible the variation acceptable range to follow the rapid fall of the pulse rate.

Also, in the 20th embodiment, in the biological information processing device according to the 14th embodiment, the variation acceptable width setting part defines the variation acceptable width as a predetermined minimum variation acceptable width when the reference pulse rate is more than a predetermined pulse rate upper limit setting value, or the reference pulse rate is less than a predetermined pulse rate lower limit setting value.

In the 20th embodiment, when the reference pulse rate is more than a predetermined pulse rate upper limit setting value, or the reference pulse rate is less than a predetermined pulse rate lower limit setting value, the variation acceptable width is defined as a predetermined minimum variation acceptable width. When the reference pulse rate is excessively high, or the reference pulse rate is excessively low, the variation acceptable width becomes smallness and there is a possibility to have an excessive narrow variation acceptable range. Thus, it is effective to define the lower limit value of the variation acceptable width, and to adjust the variation acceptable width to be more than the lower limit value.

BRIEF DESCRIPTION OF THE DRAWINGS

Referring now to the attached drawings which form a part of this original disclosure:

FIG. 5 is a table configuration drawing showing a condition definition table;
FIG. 6 is a table configuration drawing showing an appropriateness judgement table;
FIG. 9 shows a table configuration drawing for the second appropriateness judgement according to the first embodiment of the invention;
FIG. 17A shows a method for setting a window width at the time of start of exercise according to the third embodiment of the invention;
FIG. 17B shows a method for setting a window width at the time of restart of exercise from at the time of cool-down according to the third embodiment of the invention;
FIG. 17C shows a method for setting a window width at the time of stop of exercise according to the third embodiment of the invention.

DETAILED DESCRIPTION OF EXEMPLARY EMBODIMENTS

A preferred embodiment of the invention will now be described with reference to the accompanying drawings. The present embodiment is an embodiment in which the biological information processing device according to the invention is applied to a wristwatch-type pulse rate monitor. It shall be apparent that configurations in which the invention can be applied are not limited to the embodiment described below.

1. External Appearance Configuration

Figure 1:
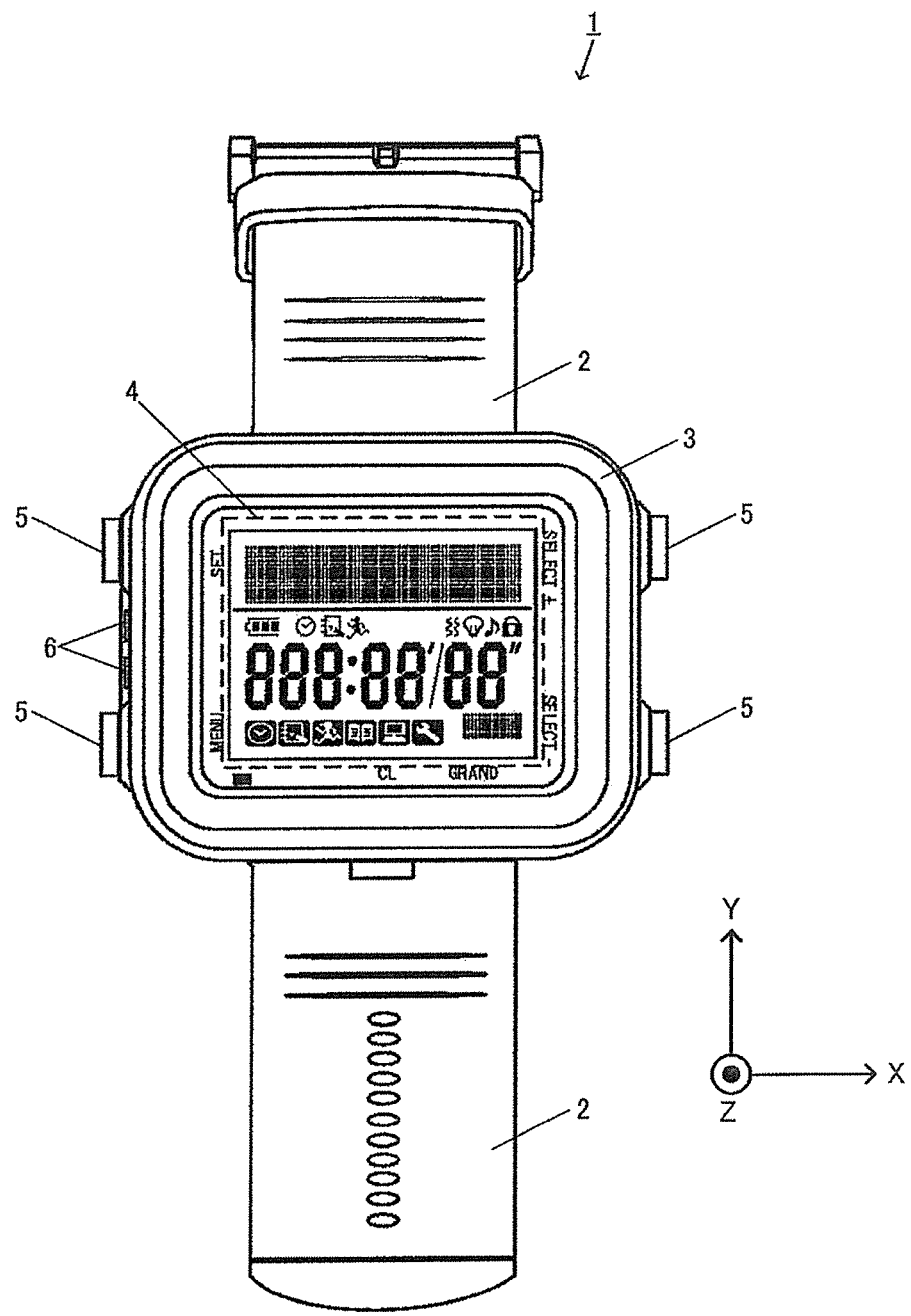
FIG. 1 is a front view of a pulse rate monitor.

FIG. 1 is a front view of a pulse rate monitor 1 according to the present embodiment. The pulse rate monitor 1 is provided with a wristband 2. A liquid crystal display 4 for displaying the time, an operation state of the pulse rate monitor 1, and a variety of biological information (e.g., pulse rate, exercise intensity, calorie consumption) using, e.g., text, numerals, or icons, is arranged on a case 3.

Operation buttons 5 used to operate the pulse rate monitor 1 are provided to a periphery section (side surface) of the case 3. The pulse rate monitor 1 operates using, e.g., an internally provided secondary cell as a power source. A charge terminal 6, used to connect with an external charger and charge the internally provided secondary cell, is provided on the side surface of the case 3.

Figures 2A, 2B:
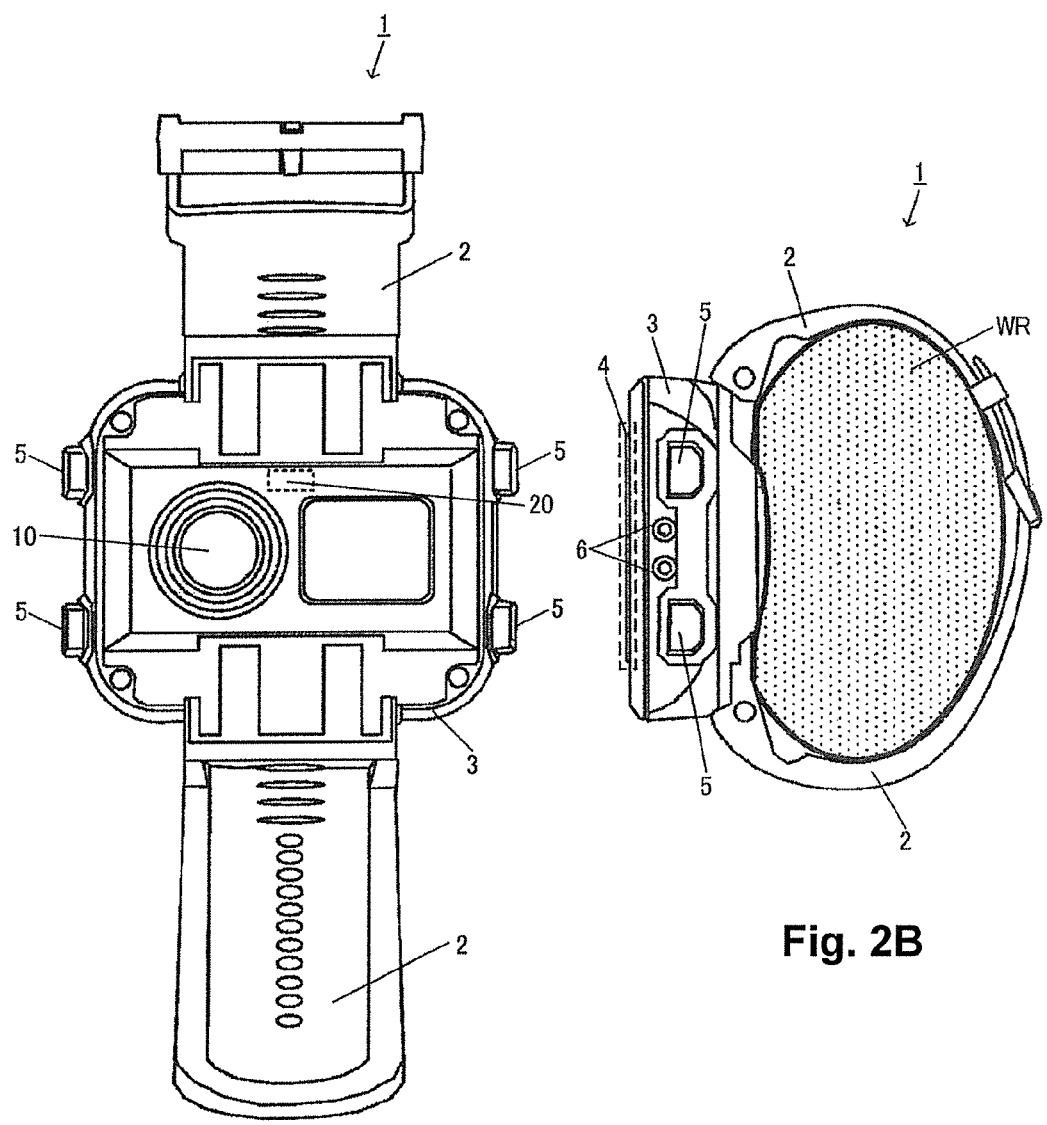
FIG. 2A is a back view of the pulse rate monitor.
FIG. 2B shows the pulse rate monitor in a state of use.

FIG. 2A is a back view of the pulse rate monitor 1, and shows an external view of the pulse rate monitor 1 when viewed from a reverse surface of the case 3. FIG. 2B shows the pulse rate monitor 1 in a state of use, and shows a side view of the pulse rate monitor 1 when in a state of being worn on the wrist WR of the test subject.

A pulse wave sensor 10 for detecting a pulse wave of the test subject and outputting a pulse wave signal is provided on the back surface of the case 3. The pulse wave sensor 10 detects the pulse wave at the wrist WR, which is in contact with the back surface of the case 3. In the present embodiment, the pulse wave sensor 10 is a photoelectric pulse wave sensor, and includes a mechanism for optical detection of the pulse wave.

Figure 3:
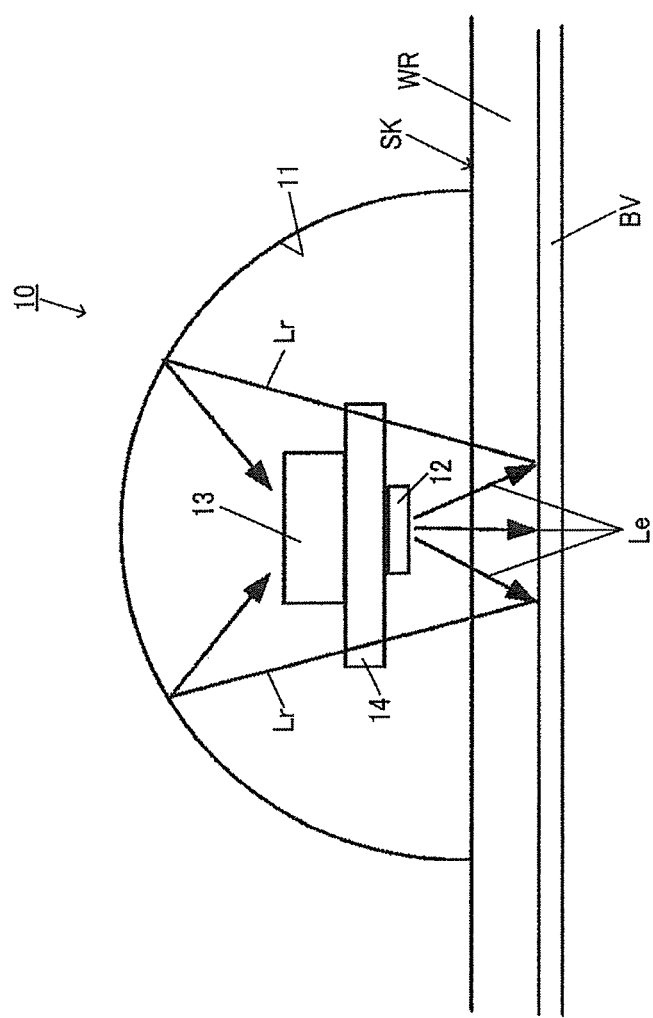
FIG. 3 illustrates the action of the pulse wave sensor.

FIG. 3 is an expanded view of an internal structure of the pulse wave sensor 10 when viewed from a side surface of the case 3. The pulse wave sensor 10 is installed in a hemispherical accommodating space having a circular bottom surface, formed on the back-surface-side of the case 3. A light-emitting diode (LED) or another light source 12 and a phototransistor or another light-receiving element 13 are internally provided within the accommodating space. An internal surface of the hemisphere is a mirror surface 11. When the bottom-surface-side of the hemisphere is defined as the downward direction, the light-receiving element 13 and the light source 12 are respectively installed on an upper surface and a lower surface of a substrate 14.

When the light source 12 emits light Le towards the skin SK of the wrist WR of the user, the emitted light Le is reflected by a blood vessel BV under the skin, and returns to within the hemisphere as reflected light Lr. The reflected light Lr is further reflected by the hemispherical reflecting surface 11, and strikes the light-receiving element 13 from above.

A light-absorbing action of hemoglobin in the blood causes the intensity of the reflected light Lr from the blood vessel BV to fluctuate so as to reflect the fluctuation in blood flow. The pulse wave sensor 10 causes the light source 12 to blink at a predetermined period that is faster than that of pulsation. Each time the light source 12 illuminates, the light-receiving element 13 outputs, through photoelectric conversion, a pulse wave signal that corresponds to the intensity of received light. The pulse wave sensor 10 causes the light source 12 to blink at a frequency of, e.g., 128 Hz.

As shown in FIG. 2A, the pulse rate monitor 1 is internally provided with a body motion sensor 20 for detecting the body motion of the test subject. In the present embodiment, the body motion sensor 20 is configured so as to have an acceleration sensor. The acceleration sensor is an acceleration sensor for three axes, namely, e.g., a z-axis oriented along a direction normal to a cover glass surface of the case 3 so that a display-surface-side is positive; a y-axis oriented along the up-down direction so that a direction oriented at 12 o'clock on a clock is positive; and an x-axis oriented along the left-right direction so that a direction oriented at 3 o'clock on the clock is positive, as shown in FIG. 1.

In a state in which the pulse rate monitor 1 is being worn, the x-axis coincides with a direction oriented from the elbow to the wrist of the test subject. The body motion sensor 20 detects acceleration along the three axes x, y, and z, and outputs a result as a body motion signal. Based on the body motion signal detected by the body motion sensor 20, the cyclic body motion of the test subject (e.g., movement of the arms or up and down movements of body) by a walking or jogging is detected.

2. First Embodiment

In the first embodiment, the pulse rate monitor 1 is indicated by the reference numeral "1001", thereby addressing each block with 1000th number. For example, the pulse wave sensor 10 is indicated by the reference numeral 1010.

2-1. Principle of the First Embodiment

The pulse rate monitor 1001 calculates the pulse rate of the test subject by using the pulse rate signal detected by the pulse rate sensor 1010. In detail, the signal intensity value (spectrum value) per frequency range is extracted upon performing a predetermined frequency analysis process to the pulse signal. For example, a Fast Fourier Transformation (FFT) can be used to apply for the frequency analysis process. Then, the frequency spectrum corresponding to the pulse wave of the test subject extracted from the signal intensity value is identified, and the pulse rate is calculated based on that frequency (or cycle). The pulse rate monitor 1001 calculates the pulse rate in a fixed time interval (for example, 1~5 sec). In the present embodiment, the pulse rate of the test subject calculated by above is indicated as a "calculated pulse rate."

The pulse rate monitor 1001 notifies the calculated pulse rate, as the results of measurement (measured pulse rate), to the test subject by displaying on the liquid crystal display 1004. However, there is a case that the measurement result of the calculated pulse rate, which is largely deviated from the real pulse rate of the test subject, is acquired, and this happens because of, for example, a disturbance effect such as changing outside temperature or a physical effect such as shifting a position of the pulse rate monitor device. In this case, the acquired pulse rate is an abnormal value, and it is not appropriate to notify this value to the test subject. Thus, an adequacy of the calculated pulse rate is judged according to the following steps in this embodiment.

First, a deviation degree between a reference pulse rate and the calculated pulse rate is determined. The reference pulse rate is a reference value of the pulse rate at the time of pulse rate calculation (calculation timing). The reference pulse rate can be arbitrarily set but in this embodiment, the latest calculated pulse rate among the calculated pulse rate determined as an appropriate is set as the reference pulse rate. Specifically, at the time when the calculated pulse rate is determined as an appropriate, process of updating the reference pulse rate based on the calculated pulse rate is repeated at every calculation event.

The deviation degree is a scale that measures how far the reference pulse rate and the calculated pulse rate have a distance. Determining the deviation degree between the reference pulse rate and the calculated pulse rate corresponds to determining the relative relationship between the reference pulse rate and the calculated pulse rate.

Figure 4:
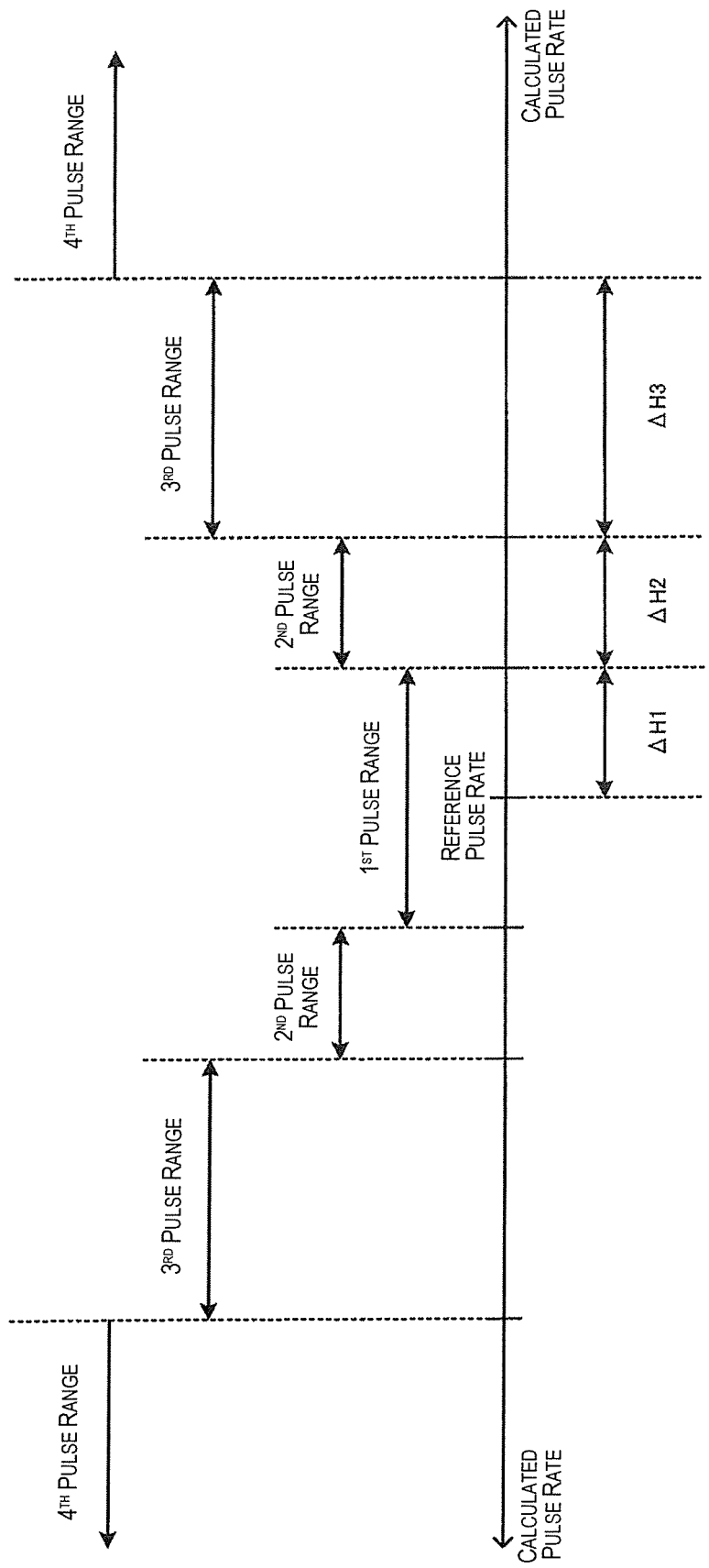
FIG. 4 shows a method for setting the pulse range.

FIG. 4 illustrates the deviation degree of the reference pulse rate and the calculated pulse rate. FIG. 4 illustrates a pulse range having an obtainable calculated pulse rate at one of the calculation timings, and a reference pulse rate is located in a center. Horizontal axis indicates the pulse rate and its center corresponds to the reference pulse rate.

As shown in FIG. 4, in a pulse range having a reference pulse rate as its center, the pulse range having a width "ΔH1" in respective lower and upper directions is set as the first pulse range. A pulse range partitioned by a width of "ΔH2" is set as a second pulse range located in an outside direction relative to the boundary of the first pulse range as a reference. A pulse range partitioned by a width of "ΔH3" is set as a third pulse range located in an outside direction relative to the boundary of the second pulse range as a reference. Also, a range other than the above ranges is set as a fourth pulse range. In addition, it is possible to arbitrarily set the values defined the ranges "ΔH1~ΔH3", and for example, it is set as "ΔH1=10 beats, ΔH2=10 beats, ΔH3=20 beats".

When a short time interval is assumed, it is rare that the pulse rate of the test subject changes rapidly in this time interval. Therefore, as the deviation degree between the reference pulse rate and the calculated pulse rate becomes smaller, a possibility for having the correct calculated pulse rate increases. However, when the test subject starts exercise or stops exercise, a situation where rapid change in pulse rate is also assumed.

Thus, in the present embodiment, the difference between the reference pulse rate and the calculated pulse rate (hereafter referred to as "pulse rate difference") is calculated, the deviation degree between the reference pulse rate and the calculated pulse rate is determined based on the pulse rate difference. On the other hand, the reliability of the calculation result of the pulse rate calculation is judged. Then, the appropriateness of the calculated pulse rate is judged based on the determined deviation degree and the determined reliability.

FIG. 5 is an explanatory drawing for the appropriateness judgment of the calculated pulse rate, and illustrates a condition definition table which defines conditions for using the appropriateness judgment. The condition definition table is provided by coordinating condition Nos. referring a number of the condition, condition items referring an item of the condition, and condition contents referring a content of the condition.

The condition A is one of the examples of the predetermined reliability condition related to the reliability of the calculated result of the pulse rate, and "SN ratio (signal to noise ratio) of the pulse wave signal>θ" is defined as the condition content. In fact, the condition defines for judging the reliability of the calculated result of the pulse rate based on the SN ratio that is the signal to noise ratio of the pulse wave signal.

The calculation of the SN ratio performs as following example. The frequency analysis process is performed to the digitized pulse wave signal (pulse wave data). Then, a base line that becomes a maximum spectrum value is selected, and this becomes a pulse base line of the test subject. Also, base lines within the predetermined peripheral range of the pulse base line are excluded, and in the excluded base lines, for example, a base line having the second largest spectrum value is selected as a noise base line. The "SN ratio=$P_S/P_N$" is calculated by using the spectrum value of the pulse base line "$P_S$" and the spectrum value of the noise base line "$P_N$".

The base lines having a large spectrum are mixed so that it is difficult to distinguish between a signal component and a noise component. In this situation, the reliability of the pulse rate calculated based on the result of the frequency analysis process is lower. In this case, the SN ratio of the pulse signal tends to be smaller. Then, a threshold value "θ" for the SN ratio is defined, and when the SN ratio exceeds the threshold value "θ", it judges that the reliability of the calculated result is high.

The condition B is a condition related to a possibility of the body motion component, and the statement "Do not exist a cyclic body motion frequency satisfying |pulse frequency−cyclic body motion frequency|<φ" is defined as a conditional content. The symbol "φ" is the threshold value of the frequency difference. This condition is an example of the predetermined frequency condition that the frequency of the cyclic body motion and the frequency of the calculated pulse rate do not approximate each other. When this frequency condition is satisfied, it determines that a possibility for catching the body motion component of the test subject in the calculated pulse rate is low.

The pulse wave signal is a signal superimposed with a pulsation component signal and a body motion noise component signal of the test subject. Thus, there is a possibility that a frequency of the cyclic body motion of the test subject (hereafter referred to as "cyclic body motion frequency") can be acquired as a pulse frequency. More specifically, the pulse rate monitor 1001 is worn on the test subject's arm, and by swinging the arm, the cyclic body motion frequency is detected as a frequency corresponding to a pitch (pace) of the test subject. Then, as a frequency condition of the appropriateness judgement, it defines that there is no existence of the cyclic body motion frequency which satisfies the predetermined approximate condition with the pulse frequency.

The frequency analysis process is performed to the body motion signal detected by the body motion sensor 1020. A basic line as a reference wave of the motion is determined by the frequency of the basic line becoming the maximum spectrum value (peak frequency) so that it determines the cyclic body motion frequency. In fact, when the frequency analysis is performed, the frequency of integral multiple of the frequency of the reference wave (harmonic frequency) tends to present a high spectrum in a basic line. Then, the harmonic frequency of the frequency of the reference wave is detected as the cyclic body motion frequency, and it is effective that the judgment in condition B is performed to these pluralities of the cyclic body motion frequency.

The condition C is a condition related to a consistency between a body movement state and a calculated pulse rate, and as conditional contents, the condition C1 is defined as that "exercise state . . . calculated pulse rate>HR1", and the condition C2 is defined as that "rest state . . . calculated pulse rate<HR2". The "HR1" is a threshold value of the calculated pulse rate in the exercise state, and the "HR2" is a threshold value of the calculated pulse rate in the rest state. These conditions are one of the examples of the consistency between the body movement state and the calculated pulse rate. In fact, it is also possible that one of the conditions C1 and C2 is only defined as a consistency condition.

The body movement state is a state of the movement related to the test subject's body, and for example, this includes an exercise state or a rest state. The body movement state can be detected based on the detection result of the body motion sensor 1020. For example, when the output of the acceleration sensor is more than the predetermined threshold value, it can be judged that the test subject is in the exercise state.

When the test subject is in the exercise state, normally, the pulse rate of the test subject should be a slightly higher. However, the calculated pulse rate may unexpectedly indicate a lower value, thus a possibility for having an incorrect calculated pulse rate increases. Also, when the test subject is in the rest state, normally, the pulse rate of the test subject should be slightly lower. However, the calculated pulse rate unexpectedly indicates a higher value, thus a possibility for having an incorrect calculated pulse rate increases. In view of the above mentioned conditions, it determines whether or not there is a discrepancy in the relative relationship between the body movement state of the test subject and the calculated pulse rate.

The condition D is a condition related to a reliability condition achieved consecutively, and "number of times that condition A is consecutively satisfied in the predetermined past time>N" is defined as a conditional content. When "the SN ratio of the pulse rate signal>θ" in the condition A is consecutively satisfied in the predetermined time period, the calculated pulse rate is determined as a reliable value.

FIG. 6 is an explanatory drawing for the appropriateness judgment of the calculated pulse rate, and illustrates an appropriateness judgment table for using the appropriateness judgment of the calculated pulse rate. The appropriateness judgment table is provided by coordinating a pulse range, a SN ratio threshold value which is a threshold value for the SN ratio, an appropriateness judgment criteria as a reference for judging the appropriateness of the calculated pulse rate.

The pulse range is defined in the 1st~4th pulse ranges as shown in FIG. 4. The SN ratio threshold value is a threshold of the reliability condition for the SN ratio of the pulse wave signal defined in the condition A of FIG. 5, and a different value is provided depending on the pulse range. In detail, as the reference pulse rate is closer to the pulse range, the SN ratio threshold value becomes smaller. However, the 1st pulse range does not define the SN ratio threshold value exceptionally. This is because when the calculated pulse rate is within the 1st pulse range, the calculated pulse rate is unconditionally determined as an appropriate.

For the other pulse ranges, the 2nd pulse range "θ2", the 3rd pulse range "θ3", and the 4th pulse range "θ4" are respectively defined as a SN ratio threshold value. The magnitude relationships of these values are "θ2<θ3<θ4". According to the calculation formula of the SN ratio as mentioned before, as the SN ratio increases its ratio, the quality of the pulse wave signal is high so that the reliability of the calculation result is also high. Therefore, setting the SN ratio threshold value to a lower number indicates relaxing the criteria that satisfies the reliability condition. In detail, in the reliability condition of the condition A, as the deviation degree between the reference pulse rate and the calculated pulse rate becomes smaller, it defines that the calculated pulse rate is easily judged as appropriate.

The appropriateness judgment criteria are the reference to judge an appropriateness of the calculated pulse rate by the appropriateness judgment. The 1st pulse range defines "every time". In detail, when the calculated pulse rate is within the 1st pulse range, the calculated pulse rate is determined as an appropriate unconditionally.

For the 2nd pulse range, "the condition A is satisfied" is defined. This means that when the condition related to the reliability of the calculated result is satisfied, the calculated pulse rate is determined as an appropriate.

For the 3rd pulse range, "(1) the conditions A & B are satisfied", "(2) the condition A is satisfied & the condition B is not satisfied & the condition D is satisfied" or "(3) the condition A is satisfied & the condition C is not satisfied & the condition D is satisfied" is defined. The calculated pulse rate within the 3rd pulse range corresponds to that the deviation degree between the reference pulse rate and the calculated pulse rate satisfies the predetermined high deviation condition.

The reference (1) means that when either one of the reliability condition or the frequency condition is satisfied, the calculated pulse rate is determined as an appropriate. In the reference (2), when the reliability condition is satisfied but the frequency condition is not satisfied; even so, if the condition related to the reliability condition achieved consecutively is satisfied, the calculated pulse rate is determined as an appropriate. This is that the judgment result in the reliability condition judgment part is the affirmative judgment, and moreover, when the judgment result of the frequency condition judgment part is negative judgment, it corresponds to the appropriateness judgment of the calculated pulse rate based on the number of times that the affirmative judgment is consecutively determined by the reliability condition judgment part.

In the reference (3), when the reliability condition is satisfied but the consistency between the body movement state and the calculated pulse rate is not satisfied; even so, if the condition related to the reliability condition achieved consecutively is satisfied, the calculated pulse rate is determined as an appropriate. This is that the judgment result of the reliability condition judgment part is the affirmative judgment, and moreover, the judgment result in the consistency condition judgment part is negative judgment, it corresponds to the judgment based on the number of times that the affirmative judgment is consecutively determined by the reliability condition judgment part.

For the 4th pulse range, it defines that all of the conditions A~D are satisfied. In detail, as long as all of the conditions A~D are not satisfied, it determines that the calculated pulse rate is improper. The 4th pulse range has the largest deviation degree between the reference pulse rate and the calculated pulse rate so that the most strict condition is defined to the appropriateness judgment of the calculated pulse rate.

2-2. Functional Configuration of the First Embodiment

Figure 7:
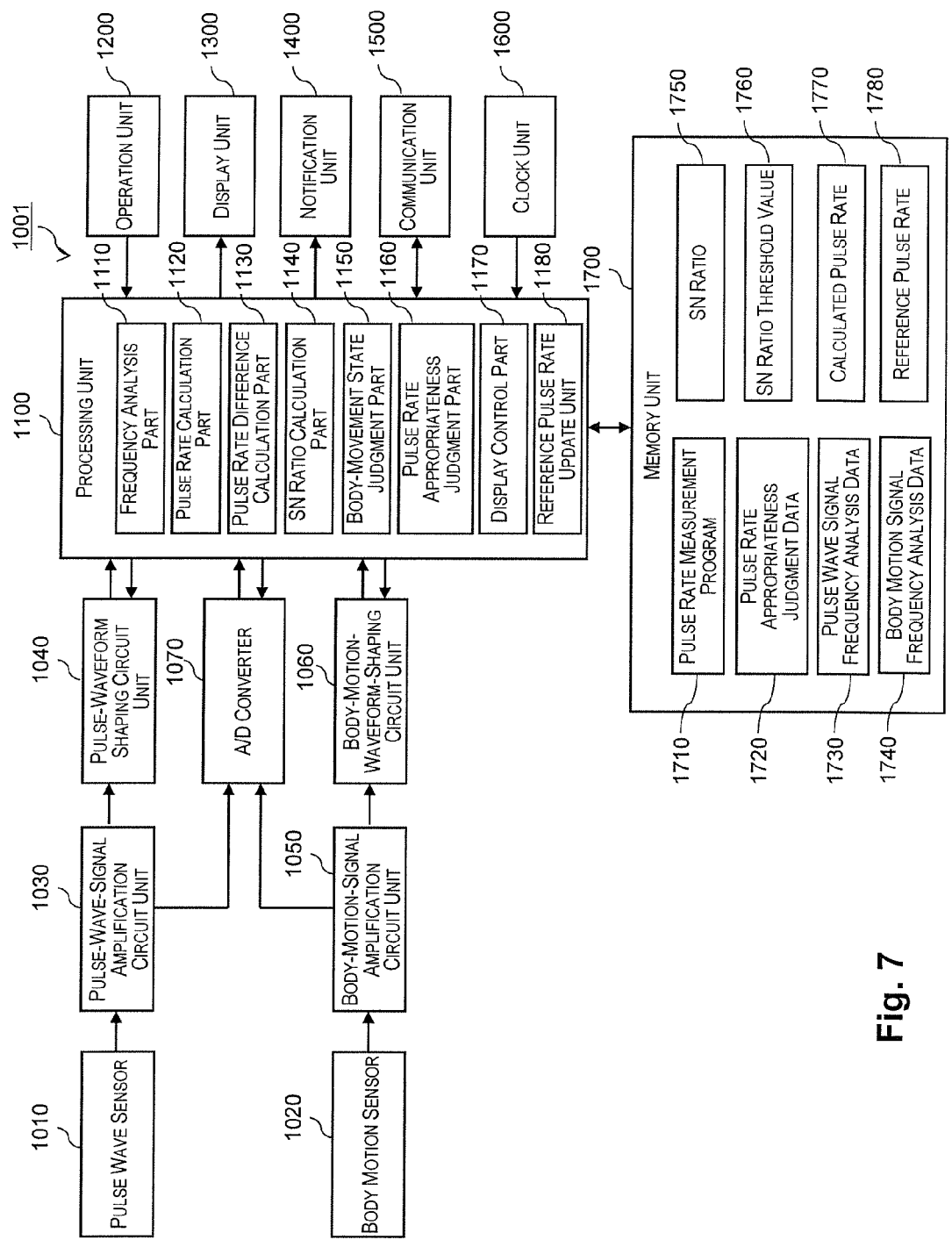
FIG. 7 is a block diagram showing the functional configuration of the pulse rate monitor according to the first embodiment of the invention.

FIG. 7 is a block diagram showing one of the examples of the functional configuration of the pulse rate monitor 1001. The pulse rate monitor 1001 includes a pulse wave sensor 1010, a body motion sensor 1020, a pulse-wave-signal amplification circuit unit 1030, a pulse-waveform shaping circuit unit 1040, a body-motion-signal amplification circuit unit 1050, a body-motion-waveform-shaping circuit unit 1060, an A/D (Analog/Digital) convertor 1070, a processing unit 1100, an operation unit 1200, a display unit 1300, a notification unit 1400, a communication unit 1500, a clock unit 1600, and a memory unit 1700.

The pulse wave sensor 1010 is a sensor for detecting a pulse wave signal having the pulse wave of the test subject who wears the pulse rate monitor 1001. For example, the sensor is configured so as to have a photoelectric pulse wave sensor. The pulse wave sensor 1010 detects, as a pulse wave signal, a change in volume generated by inflow of blood into a body tissue, and outputs the pulse wave signal to the pulse-wave-signal amplification circuit unit 1030.

The pulse-wave-signal amplification circuit unit 1030 is an amplification circuit for amplifying, by a predetermined gain, the pulse wave signal inputted from the pulse wave sensor 1010. The pulse-wave-signal amplification circuit unit 1030 outputs the amplified pulse wave signal to the pulse-waveform shaping circuit unit 1040 and the A/D converter 1070.

The pulse-waveform shaping circuit unit 1040 is a circuit unit for shaping the pulse wave signal that has been amplified by the pulse-wave-signal amplification circuit unit 1030, and is configured so as to have a circuit for removing a high-frequency noise component, a clipping circuit, and other elements. The processing unit 1100 judges, on the basis of a pulse waveform that has been shaped by the pulse-waveform shaping circuit unit 1040, whether or not a pulse wave has been detected.

The body motion sensor 1020 is a sensor for establishing the movement of the test subject wearing the pulse rate monitor 1001, and is configured so as to have at least an acceleration sensor. The body motion sensor 1020 corresponds to a body-motion-detector for detecting the body motion of the test subject.

The body-motion-signal amplification circuit unit 1050 is an amplification circuit for amplifying, by a predetermined gain, the body motion signal inputted from the body motion sensor 1020. The body-motion-signal amplification circuit unit 1050 outputs the amplified body motion signal to the body-motion-waveform-shaping circuit unit 1060 and the A/D converter 1070.

The body-motion-waveform-shaping circuit unit 1060 is a circuit unit for shaping the body motion signal that has been amplified by the body-motion-signal amplification circuit unit 1050, and is configured so as to have a circuit for removing a high-frequency noise component, a circuit for differentiating between a gravitational acceleration component and other components, a clipping circuit, and other elements. The processing unit 1100 judges, on the basis of a body motion waveform shaped by the body-motion-waveform-shaping circuit unit 1060, whether or not body motion has been detected.

The A/D converter 1070 samples and digitizes, at predetermined sampling time intervals, and converts to a digital signal, each of the analog pulse wave signal amplified by the pulse-wave-signal amplification circuit unit 1030 and the analog body motion signal amplified by the body-motion-signal amplification circuit unit 1050. Then, the A/D converter 1070 outputs the converted digital signal to the processing unit 1100.

The processing unit 1100 is a control device and a computation device for performing overall control of each of the units of the pulse rate monitor 1001 according to a variety of programs, such as a system program, stored in the memory unit 1700, and is configured so as to have a processor such as a central processing unit (CPU) or DSP (Digital Signal Processor). The processing unit 1100 performs a first pulse rate measurement process according to a pulse rate measurement program 1710 stored in the memory unit 1700, and performs a control so that the pulse rate of the test subject wearing the pulse rate monitor 1001 is calculated/measured and displayed on the display unit 1300.

The processing unit 1100 includes, for example, a frequency analysis part 1110, a pulse rate calculation part 1120, a pulse rate difference calculation part 1130, a SN ratio calculation part 1140, a body movement state judgement part 1150, a pulse rate appropriateness judgement part 1160, a display control part 1170, and a reference pulse rate update unit 1180. However, these functional parts are one of the examples so that this does not always require configuring all of the functional parts.

The frequency analysis part 1110 acquires the frequency spectrum of the pulse signal by performing a frequency analysis process such as FFT for the pulse signal (pulse wave data) input from the A/D converter 1070. Also, the frequency analysis part 1110 acquires the frequency spectrum of the body motion signal by performing the frequency analysis process such as FFT for the body motion signal (body motion data) input from the A/D converter 1070. The frequency analysis part 1110 corresponds to a body motion frequency judgement part to judge the frequency of the body motion of the test subject by using the detected results of the body motion detection part.

The pulse rate calculation part 1120 detects the frequency spectrum corresponding to the pulse wave of the test subject from the frequency spectrum of the pulse signal acquired by the frequency analysis part 1110, and calculates the pulse rate based on the frequency (or cycle). The pulse rate calculation part 1120 corresponds to a pulse rate calculation part which calculates the pulse rate of the test subject.

The pulse rate difference calculation part 1130 calculates the difference (pulse rate difference) between the reference pulse rate 1780 and the calculated pulse rate 1770 stored in the memory unit 1700. The pulse rate difference calculation part 1130 corresponds to a deviation degree judgement part to judge a degree of deviation of the calculated pulse rate calculated by the given reference pulse rate and the pulse rate calculation part.

The SN ratio calculation part 1140 calculates the SN ratio 1750 of the pulse wave signal based on the frequency rate analysis results of the pulse wave signal analysed by the frequency analysis part 1110. The SN ratio calculation part 1140 corresponds to a reliability judgement part for judging reliability of the calculated results in the pulse rate calculation part.

The body movement state judgement part 1150 judges a body movement state of the test subject based on the detected results in the body motion sensor 1020. The body movement state judgement part 1150 corresponds to a body movement state judgement part for judging the body movement state of the test subject by using the results of the detection in a body movement detection part.

The pulse rate appropriateness judgement part 1160 is an appropriateness judgement part for judging an appropriateness of the calculated pulse rate 1770, by reviewing the pulse rate appropriateness judgement data 1720 stored in the memory unit 1700, according to the above principle. The pulse rate appropriateness judgement part 1160 includes a reliability conditions judgement part (not shown in the drawings) to determine whether or not the predetermined reliability conditions are satisfied, and the predetermined reliability conditions are defined such that as the deviation degree becomes smaller, it tends to determine that the calculated pulse rate is appropriate. Also, the pulse rate appropriateness judgement part 1160 includes a frequency conditions judgment part to determine whether or not the predetermined frequency conditions, a frequency of the body motion cycle does not approximate a frequency of the calculated pulse rate, are satisfied, and a matching conditions judgment part to determine whether or not the body movement state and the calculated pulse rate satisfy the predetermined matching conditions.

The display control part 1170 displays the pulse rate based on the results of the pulse rate appropriateness judgment part 1160 on the display unit 1300. In detail, when the pulse rate appropriateness judgment part 1160 determines that the calculated pulse rate 1770 is appropriate, the calculated pulse rate 1770 is displayed as the measured pulse rate (result measurement) on the display unit 1300. On the other hand, when the pulse rate appropriateness judgment part 1160 determines that the calculated pulse rate 1770 is improper, the latest reference pulse rate 1780 is displayed as the measured pulse rate (result measurement) on the display unit 1300.

When the pulse rate appropriateness judgment part 1160 determines that the calculated pulse rate 1770 is appropriate, the reference pulse rate update part 1180 updates the reference pulse rate 1780 in accordance with the calculated pulse rate 1770.

The operation unit 1200 is configured so as to have button switches as an input device, and outputs a signal corresponding to a pressed button to the processing unit 1100. The operation unit 1200 is operated to input a variety of commands, such as a command for measuring the pulse rate. The operation unit 1200 corresponds to the operation buttons 5 shown in FIG. 1.

The display unit 1300 is a display device configured so as to have a liquid crystal display (LCD) and other elements and used for performing a variety of displays on the basis of a display signal inputted from the processing unit 1100. The display unit 1300 displays a variety of biological information (pulse rate, exercise intensity, calorie consumption, etc.). The display unit 1300 corresponds to the liquid crystal display 4 shown in FIG. 1.

The notification unit 1400 is a notification device configured so as to have a speaker, a piezoelectric vibrator, or a similar device, and used for performing a variety of notifications based on a notification signal inputted from the processing unit 1100. The notification unit 1400 performs a variety of notifications for the benefit of the test subject by, e.g., outputting an alarm sound from a speaker or causing a piezoelectric vibrator to vibrate.

The communication unit 1500 is a communication device for transmitting/receiving, in accordance with a control performed by the processing unit 1100, information used within a device, with respect to a personal computer (PC) or another external information processing device. A variety of methods can be applied as a communication method for the communication unit 1500, such as a format in which a wired connection is established through a cable that conforms to predetermined communication standards, a format in which a connection is established using an intermediate device known as a cradle that also functions as a charger, or a format in which a wireless connection is established using near field communication.

The clock unit 1600 is a time-measuring device configured so as to have a device such as a crystal oscillator including a crystal unit and an oscillation circuit, and used for measuring the time. The time measured by the clock unit 1600 is continually outputted to the processing unit 1100.

The memory unit 1700 is configured by read-only memory (ROM), flash ROM, random-access memory (RAM), or another memory device. The memory unit 1700 stores a system program of the pulse rate monitor 1001, and other programs, data for realizing a pulse rate measurement function, exercise intensity measurement function, calorie measurement function, and other functions. The memory unit 1700 also has a work area for temporarily storing mid-process data, processing results relating to a variety of processes.

As a program, the memory unit 1700 stores a pulse rate measurement program 1710 to execute the first pulse rate measurement process (shown in FIG. 8) processed by the processing unit 1100. As a data, the memory unit 1700 also stores pulse rate appropriateness judgment data 1720, pulse wave signal frequency analysis data 1730, body motion signal frequency analysis data 1740, a SN ratio 1750, a SN ratio threshold value 1760, a calculated pulse rate 1770, and a reference pulse rate 1780.

The pulse rate appropriateness judgment data 1720 is data to be used for the appropriateness judgment of the calculated pulse rate 1770 in the pulse rate appropriateness judgment part 1160. For example, the data includes the conditions definition table as explained in FIG. 5 or the table used for the appropriateness judgement as explained in FIG. 6.

The pulse rate signal frequency analysis data 1730 is data for the signal intensity value (spectrum value) of each band of the frequencies acquired by performing the frequency analysis process for the pulse wave signal in the frequency analysis part 1110. In a similar fashion, the body motion signal frequency analysis data 1740 is data for the signal intensity value (spectrum value) of each band of the frequencies acquired by performing the frequency analysis process for the body motion signal in the frequency analysis part 1110.

2-3. Process Flow of the First Embodiment

Figure 8:
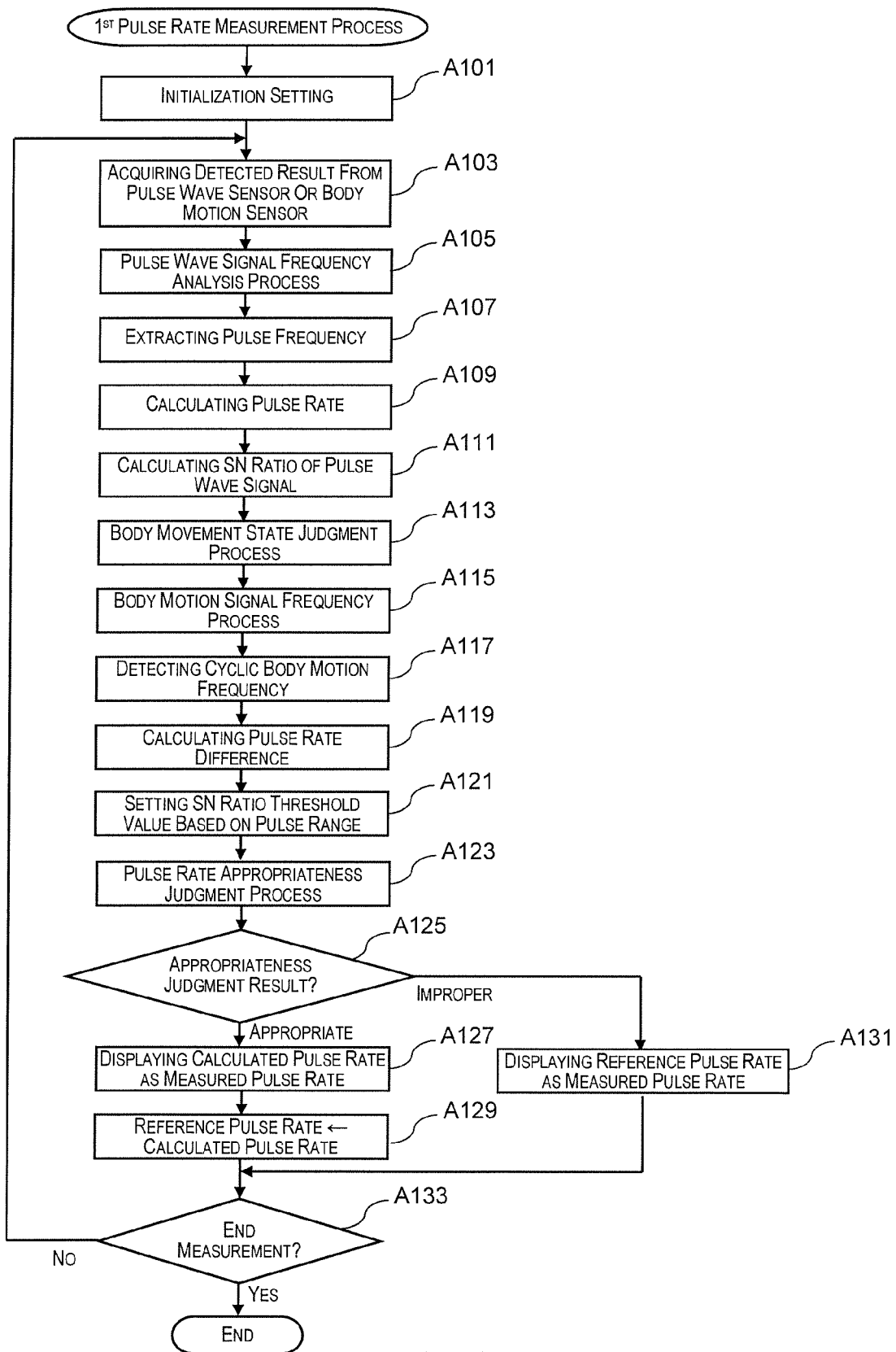
FIG. 8 is a flow chart showing the flow of the first pulse rate measurement process according to the first embodiment of the invention.

FIG. 8 is a flow chart showing the first pulse rate measurement process executed in the pulse rate monitor 1001 due to the pulse rage measurement program 1710 stored in the memory unit 1700 being read by the processing unit 1100.

First, the processing unit 1100 performs initialization setting (step A101). For example, a predetermine value is set as an initial value of the reference pulse rate 1780 (e.g., rest pulse rate).

Next, the processing unit 1100 acquires the results detected by the pulse wave sensor 1010 and the body motion sensor 1020 (step A103). Then, the frequency analysis part 1110 performs a frequency analysis process to the pulse signal detected by the pulse wave sensor 1010, and the result is stored in the memory unit 1700 as a pulse wave signal frequency analysis data 1730 (step A105).

Next, the pulse rate calculation part 1120 extracts a pulse frequency by using the pulse wave signal frequency analysis data 1730 (step A107). Then, the pulse rate calculation part 1120 calculates the pulse rate of the test subject based on the extracted pulse rate, and the calculated pulse rate 1770 of the memory unit is updated by using the calculated result (step A109).

The SN ratio calculation part 1140 calculates the SN ratio 1750 of the pulse wave signal by using the pulse wave signal frequency analysis data 1730, and the result is stored in the memory unit 1700 (step A111). The body movement state judgment part 1150 performs a body movement judgment process to judge the body movement state of the test subject based on the result of the determination of the body motion sensor 1020 (step A113).

After that, the frequency analysis part 1110 performs a frequency analysis process to the body motion signal detected by the body motion sensor 1020, and the result is stored in the memory unit 1700 as body motion signal frequency analysis data 1740 (step A115). Then, the frequency analysis part 1110 detects a body motion frequency cycle based on the frequency analysis result (step A117).

After that, the pulse rate difference calculation part 1130 calculates the difference (pulse rate difference) between the reference pulse rate 1780 and the calculated pulse rate 1770 (step A119). Then, the processing unit 1100 sets, by review a table for a pulse rate appropriateness judgment (shown in FIG. 6) included in the pulse rate appropriateness judgment data 1720, the SN rate threshold value 1760 in a predetermined pulse range for the pulse rate difference (step A121).

Then, the pulse rate appropriateness judgement part 1160 performs a pulse rate appropriateness judgement process to judge an appropriateness of the calculated pulse rate 1770 (step A123). In detail, the pulse rate appropriateness judgement part 1160 judges, by reviewing a conditions definition table (shown in FIG. 5) and a table for an appropriateness judgement (shown in FIG. 6), whether or not an appropriateness judgement criteria in the predetermined pulse range is satisfied.

When the result of the appropriateness judgement is appropriate (step A125; appropriate), the display control part 1170 displays the calculated pulse rate as measured pulse rate on the display unit 1300 (step A127). Then, the reference pulse rate update part 1180 updates the reference pulse rate 1780 of the memory unit 1700 by using the calculated pulse rate 1770 (step A129). On the other hand, when the result of the appropriateness judgement is improper (step A125; improper), the display control part 1170 displays the reference pulse rate 1780 as measured pulse rate on the display unit 1300 (step A131).

After steps A129 or A131, the processing unit 1100 judges whether or not the pulse rate measurement is ending (step A133). For example, the processing unit 1100 judges whether or not the test subject operates that the pulse rate measurement is ending through the operation unit 1200. Then, when the processing unit 1100 judges that the measurement is not ending (step A133; No), it returns to step 103. Also, when the processing unit 1100 judges that the measurement is ending (step A133; Yes), the first pulse rate measurement process is completed.

2-4. Effect of the First Embodiment

In the pulse rate monitor 1001, the pulse rate calculation part 1120 calculates the pulse rate of the test subject based on the determination result of the pulse wave sensor 1010. Also, the pulse rate difference calculation part 1130 calculates the difference (pulse rate difference) between the reference pulse rate and the calculated pulse rate, and the deviation degree between the reference rate and the calculated pulse rate is judged based on the pulse rate difference. The SN ratio calculation part 1140 calculates the SN ratio of the pulse signal detected by the pulse wave sensor 1010, and the reliability of the calculated result of the pulse rate calculation part 1120 is judged based on the SN ratio. Then, the pulse rate appropriateness judgment part 1160 judges an appropriateness of the calculated pulse rate based on the pulse rate difference (deviation degree) calculated by the pulse rate difference calculation part 1130 and the SN ratio (reliability) calculated by the SN ratio calculation part 1140.

The pulse rate difference is a scale that measures how far the reference pulse rate and the calculated pulse rate have a distance. Normally, it is a rare situation that the pulse rate of the test subject changes rapidly in a short time interval. Thus, to some degree, the correctness of the calculated pulse rate calculated by the pulse rate calculation part 1120 can be determined from the deviation degree between the reference pulse rate and the calculated pulse rate. On that basis, by reviewing the SN ratio calculated by the SN ratio calculation part 1140, it is possible to perform the appropriateness judgment of the calculated pulse rate correctly.

Based on the pulse rate difference (deviation degree) and the SN ratio (reliability), it defines that as the pulse rate difference becomes smaller, the calculated pulse rate is easily judged as appropriate. In this condition, the pulse rate appropriateness judgment part 1160 judges whether or not the predetermined reliability condition is satisfied. In detail, as the pulse rate difference becomes smaller pulse range, the threshold value is set lower for the SN ratio. By these configurations, it is possible to perform the appropriateness judgment of the calculated pulse rate in accordance with the proper reliability condition depending on the deviation degree between the reference pulse rate and the calculated pulse rate.

2-5. Modification Example of the First Embodiment

The modification example of the first embodiment will now be described.

2-5-1. Biological Information Processing Device

In the first embodiment, a description was given using a wristwatch-type pulse rate monitor as an example of a biological information processing device; however, a biological information processing device to which the invention can be applied is not limited to that described. For example, the invention can also be applied to a finger-worn pulse rate monitor, which is worn on the finger when the pulse rate is measured. The method for detecting the pulse wave signal is not limited to a detection method in which light is used; a detection method in which ultrasound is used, or a detection method in which cardiograph is used, is also possible.

2-5-2. Body-Motion-Detector

In the first embodiment, it was described that the body motion sensor, which is the body-motion-detector, is configured so as to have an acceleration sensor. However, the body motion sensor can also be configured so as to have another sensor instead of an acceleration sensor. For example, the body motion sensor can be configured so as to have a gyro sensor, and the body motion of the test subject is detected based on the angular velocity detected by the gyro sensor. Of course, the body motion sensor can be configured so as to have both the acceleration sensor and the gyro sensor, and by using the results detected by these sensors, the body motion of the test subject can be detected.

2-5-3. Deviation Degree

Instead of the judgment based on the difference (pulse rate difference) between the reference pulse rate and the calculated pulse rate, the deviation degree between the reference pulse rate and the calculated pulse rate can be determined based on for example, the ratio (pulse ratio) between the reference pulse rate and the calculated pulse rate. In detail, it can be acceptable, as long as the deviation degree is a barometer for judging the relative relationship between the reference pulse rate and the calculated pulse rate.

2-5-4. Condition for the Appropriateness Judgment

The condition definition table for defining the conditions as shown in FIG. 5, and the appropriateness judgment table for defining the appropriateness judgment criteria as shown in FIG. 6 are one of the examples so that it is possible to set arbitrary. For example, the appropriateness judgment table can be defined as follows.

FIG. 9 illustrates a configuration of the second appropriateness judgment table as a modification example. In the second appropriateness judgment table, "θ1" is defined as the SN ratio threshold value of the 1st pulse range, and "the condition A is satisfied" is defined as the appropriateness judgment criteria. Also, "θ2" is defined as the SN ratio threshold value of the 2nd pulse range, and "(1) the conditions A & B are satisfied" or "(2) the conditions A is satisfied & the condition B is not satisfied & the condition D is satisfied" is defined as the appropriateness judgment criteria.

In addition, "θ3" is defined as the SN ratio threshold value of the 3rd pulse range, and "(1) the conditions A & B & C are satisfied", "(2) the conditions A & B are satisfied & the condition C is not satisfied & the condition D is satisfied" or "(3) the conditions A & C are satisfied & the condition B is not satisfied & the condition D is satisfied" is defined as the appropriateness judgment criteria. Furthermore, the value is not defined as the SN ratio threshold value of the 4th pulse range, and "No judgment as an appropriate" is defined as the appropriateness judgment criteria.

The magnitude relationship of the SN ratio threshold values is defined in accordance with the same table as the first appropriateness judgment table as shown in FIG. 6. In fact, as the deviation degree between the reference pulse rate and the calculated pulse rate becomes smaller, the calculated pulse rate is easily judged as an appropriate. As the pulse range is close to the reference pulse rate, a smaller value is set as the SN ratio threshold value. In detail, the smaller or larger relationship of the SN ratio threshold values is "θ1<θ2<θ3".

Also, in a similar manner as described in the first appropriateness judgment table, as the deviation degree between the reference pulse rate and the calculated pulse rate becomes larger, the appropriateness judgment criteria is strictly provided to judge the calculated pulse rate as an appropriate. Specifically, in the 4th pulse range, nevertheless the achievement of the conditions A~D, it is defined to always judge that the calculated pulse rate is improper.

In the first embodiment, a description was given using the number of the stages such as 4 stages of the pulse rate; however, a method of setting the number of the pulse range stages or the pulse range to which the invention can be applied is not limited to that described.

2-5-5. Reliability of the Calculated Result of the Pulse Rate

In the first embodiment, the reliability of the calculated result of the pulse rate is determined based on the SN ratio (Signal to Noise ratio) of the pulse signal detected by the pulse wave sensor 1010. However, the SN ratio is only one of the scales for the reliability judgment, and it can be also possible to use other scales for the reliability judgment.

For example, the calculated result based on the pulse wave signal intensity can be used for the reliability judgment. In detail, when the amplitude of the pulse rate is extremely small, a possibility for not acquiring the pulse rate of the test subject increases so that the reliability of the calculated pulse rate can be determined as low. Also, when the pulse wave signal is suddenly scaled out, a possibility for mixing the noise increases so that in this case, also, the reliability of the calculated pulse rate can be determined as low.

In this case, regarding the condition A of the condition definition table as shown in FIG. 5, the condition related to the reliability of the result of the calculated pulse rate can be defined, for example, depending on the signal intensity of the pulse wave signal. Also, a condition which is the combination of the SN ratio of the pulse signal and the signal intensity can be defined as the reliability condition.

2-5-6. Reference Pulse Rate

In the first embodiment, it describes that the latest calculated pulse rate, which is determined as an appropriate in the appropriateness judgment, is set as the reference pulse rate. In detail, at the time when the calculated pulse rate is determined as an appropriate, process of updating the reference pulse rate based on the calculated pulse rate is repeated per every calculation time.

However, the pulse rate, which is possible to be set as a reference pulse rate, is not limited to that described. For example, an average value or a central value of the calculated pulse rate, which was determined as an appropriate in a period from the current calculating time to the predetermined past time (e.g., 5 calculating times in the past period), can be calculated and set as a reference pulse rate.

3. Second Embodiment

In the first embodiment, the pulse rate monitor 1 is indicated by the reference numeral "2001", thereby addressing each block with 2000th number. For example, the pulse wave sensor 10 is indicated by the reference numeral 2010.

3-1. Principle of the Second Embodiment

The pulse rate monitor 2001 calculates the pulse rate of the test subject by using the pulse rate signal detected by the pulse rate sensor 2010. In detail, the signal intensity value (spectrum value) per frequency range is extracted upon performing a predetermined frequency analysis process to the pulse signal. For example, a Fast Fourier Transformation (FFT) can be used to apply for the frequency analysis process. Then, the frequency spectrum corresponding to the pulse wave of the test subject extracted from the signal intensity value is identified, and the pulse rate is calculated based on that frequency (or cycle). The pulse rate monitor 2001 calculates the pulse rate in a fixed time interval (for example, 1~5 sec). In the present embodiment, the pulse rate of the test subject calculated by above is indicated as a "calculated pulse rate."

The pulse rate monitor 2001 notifies the calculated pulse rate, as the results of measurement (measured pulse rate), to the test subject by displaying on the liquid crystal display 2004. However, there is a case that the measurement result of the calculated pulse rate, which is largely deviated from the real pulse rate of the test subject, is acquired, and this happens because of, for example, a disturbance effect such as changing outside temperature or a physical effect such as shifting a position of the pulse rate monitor device 2001. In this case, the acquired pulse rate is an abnormal value, and it is not appropriate to notify this value to the test subject. Thus, an adequacy of the calculated pulse rate is judged according to the following steps in this embodiment.

In this embodiment, a range having the same width in higher and lower directions on the basis of the predetermined reference pulse rate is defined as a window. The reference pulse rate is a reference value of the pulse rate at the time of pulse rate calculation (calculation timing). In this embodiment, the latest calculated pulse rate determined as an appropriate by the appropriateness judgment is set as the reference pulse rate. Specifically, at the time when the calculated pulse rate is determined as an appropriate, process of updating the reference pulse rate based on the calculated pulse rate is repeated per every calculation time.

For the respective calculation times, it determines whether or not the calculated pulse rate is within the window. Then, when the calculated pulse rate is within the window, the calculated pulse rate is determined as an appropriate. On the other hand, when the calculated pulse rate is not within the window, the calculated pulse rate is determined as an improper. The window is a range, which allows the variation of the calculated pulse rate (hereinafter referred to as "variation acceptable range") calculated on the basis of the predetermined reference pulse rate.

In the present embodiment, it counts the number of times that the improperness is consecutively judged for the calculated pulse rate determined by the appropriateness judgment of the above pulse rate. As the value becomes larger, the window width increases for the reference pulse rate.

The symbol "W" is indicated as the window width as described below. Also, the symbol "N" is indicated as the number of times that the improperness is consecutively judged, and the window width "$W=W_0$" in case "$N=0$" is called "initial window width". Also, the symbol "t" is indicated as the calculation timing of the pulse rate.

Figure 10:
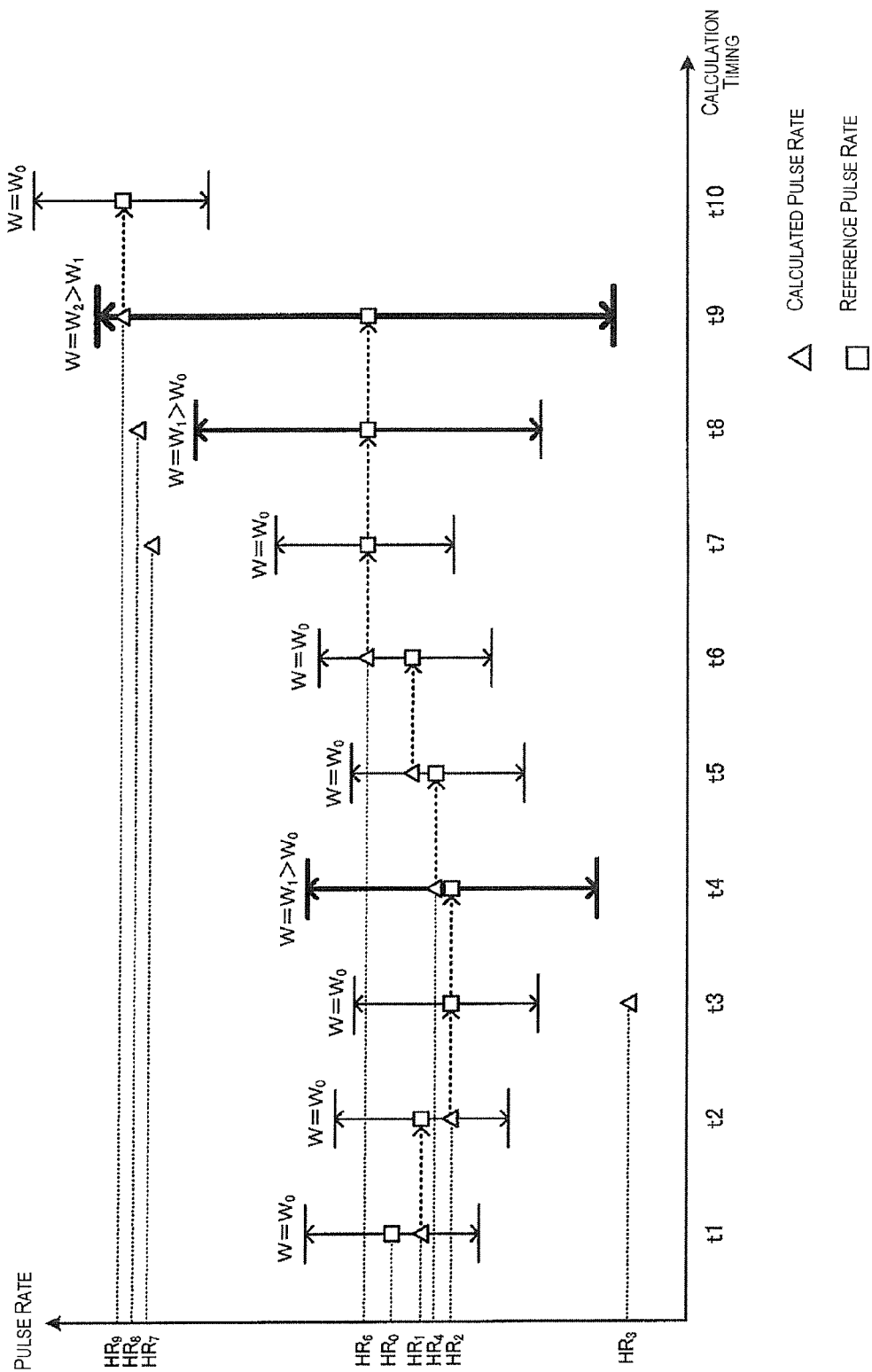
FIG. 10 shows an appropriateness judgement method of a calculated pulse rate according to the second embodiment of the invention.

FIG. 10 illustrates an appropriateness judgment method for the calculated pulse rate in the present embodiment. In FIG. 10, the horizontal axis is a time axis, and the disaggregate calculation timing "t" is shown below the time axis. The longitudinal axis is an axis of the pulse rate. Also, a calculated pulse rate is indicated as a triangle plot, and a reference pulse rate is indicated as a rectangular plot.

The reference pulse rate in the calculation timing "t1" is "$HR_0$", and the window width starts from a state in the initial window width "$W_0$". In detail, the window at the calculation timing "t1" is defined as a variation acceptable range having its center set as the reference pulse rate "$HR_0$" and its width set as the initial window width "$W_0$". In FIG. 10, the calculated pulse rate at the calculation timing "t1" is "$HR_1(<HR_0)$", and the value is within the window. Therefore, the calculated pulse rate "$HR_1$" is determined as an appropriate. The number of times "N" that the improperness is consecutively judged remains at "0 time", therefore it does not update. Also, the reference pulse rate is updated by the calculated pulse rate "$HR_1$".

In the calculation timing "t2", the window is set in the calculated pulse rate "$HR_1$" as a reference. Since the number of times is "$N=0$", the window having its center set as the reference pulse rate "$HR_1$" and its width set as the initial window width "$W_0$" is defined. In FIG. 10, the calculated pulse rate at the calculation timing "t2" is "$HR_2(<HR_0)$", and it is within the window. Therefore, the calculated pulse rate "$HR_2$" is determined as an appropriate. The number of times "N" that the improperness is consecutively judged remains "0 time" and it does not update. Also, the reference pulse rate is updated by the calculated pulse rate "$HR_2$".

In the calculation timing "t3", the window is set in the calculated pulse rate "$HR_2$" as a reference. Since the number of times is "$N=0$", the window having its center set as the reference pulse rate "$HR_2$" and its width set as the initial window width "$W_0$" is defined. In FIG. 10, the calculated pulse rate "$HR_3(<HR_2)$" at the calculation timing "t3", which is largely deviated from the real pulse rate of the test subject, is acquired. In this case, the calculated pulse rate "$HR_3$" is not within the window so that it is determined as improper. Moreover, since the value was determined as improper, the number of times "N" that the improperness is consecutively judged is updated to "1 time". The reference pulse rate remains "$HR_2$" and it does not update.

In the calculation timing "t4", the window is set in the calculated pulse rate "$HR_2$" as a reference. Since the number of times is "$N=1$", the window width "$W_1(>W_0)$", which is wider than the window width "$W_0$", is defined. In FIG. 10, the calculated pulse rate "$HR_4(<HR_3)$" at the calculation timing "t4" is within the window so that the calculated pulse rate "$HR_4$" is determined as an appropriate. Since it was determined as an appropriate, the number of times "N" that the improperness is consecutively judged resets "0 time". Also, the reference pulse rate is updated by the calculated pulse rate "$HR_4$".

Hereinafter, the similar procedure is used for the appropriateness judgment of the calculated pulse rate. In FIG. 10, at the calculation timing "t7", the pulse rate of the test subject shows a rapid raise from "$HR_6$" to "$HR_7$". In this case, at the calculation timing "t7", the window cannot follow the rapid raise of the pulse rate, therefore the window is outside from the calculated pulse rate "$HR_7$". Therefore, the calculated pulse rate "$HR_7$" is determined as improper, and the number of times "N" that the improperness is consecutively judged is updated to "1 time".

Since the number of times is "N=1", at the next calculation timing "t8", the window having its center set as the reference pulse rate "$HR_6$" and its width set as the window width "$W_1(>W_0)$" is determined. In this time, the calculated pulse rate "$HR_8(<HR_7)$" is acquired at the calculation timing "t8". Even though the window was stretched, the figure shows that the window could not acquire the calculated pulse rate "$HR_8$". In this case, the calculated pulse rate "$HR_8$" is determined as improper, and the number of times "N" that the improperness is consecutively judged is updated to "2 times".

Since the number of times is "N=2", at the next calculation timing "t9", the window having its center set as the reference pulse rate "$HR_6$" and its width set as the window width "$W_2(>W_1)$" is determined. In detail, the window, which is wider than the window set at the calculation timing "t8", is defined. In FIG. 10, the calculated pulse rate "$HR_9(>HR_8)$" is acquired at the calculation timing "t9". By the result of the stretched window, the calculated pulse rate "$HR_9$" is determined as an appropriate. Therefore, the number of times "N" that the improperness is consecutively judged resets to "0 time".

As stated above, in the present embodiment, this is one of the features that as the value of the number of times that the improperness is consecutively judged increases, the window width increases its range. At the calculation timing "t3", even if the value of the calculated pulse rate, which is largely deviated from the real pulse rate, is acquired, the judgment that an abnormal value is incorrectly determined as an appropriate is avoided because the window is set narrower at first. Also, even if the pulse rate of the test subject has changed rapidly, it is possible to judge the calculated pulse rate as an appropriate at the early stage because the window is stretching every time that the calculated pulse rate is determined as improper. That is to say the appropriate calculated pulse rate can be acquired at the early stage.

Figure 11:
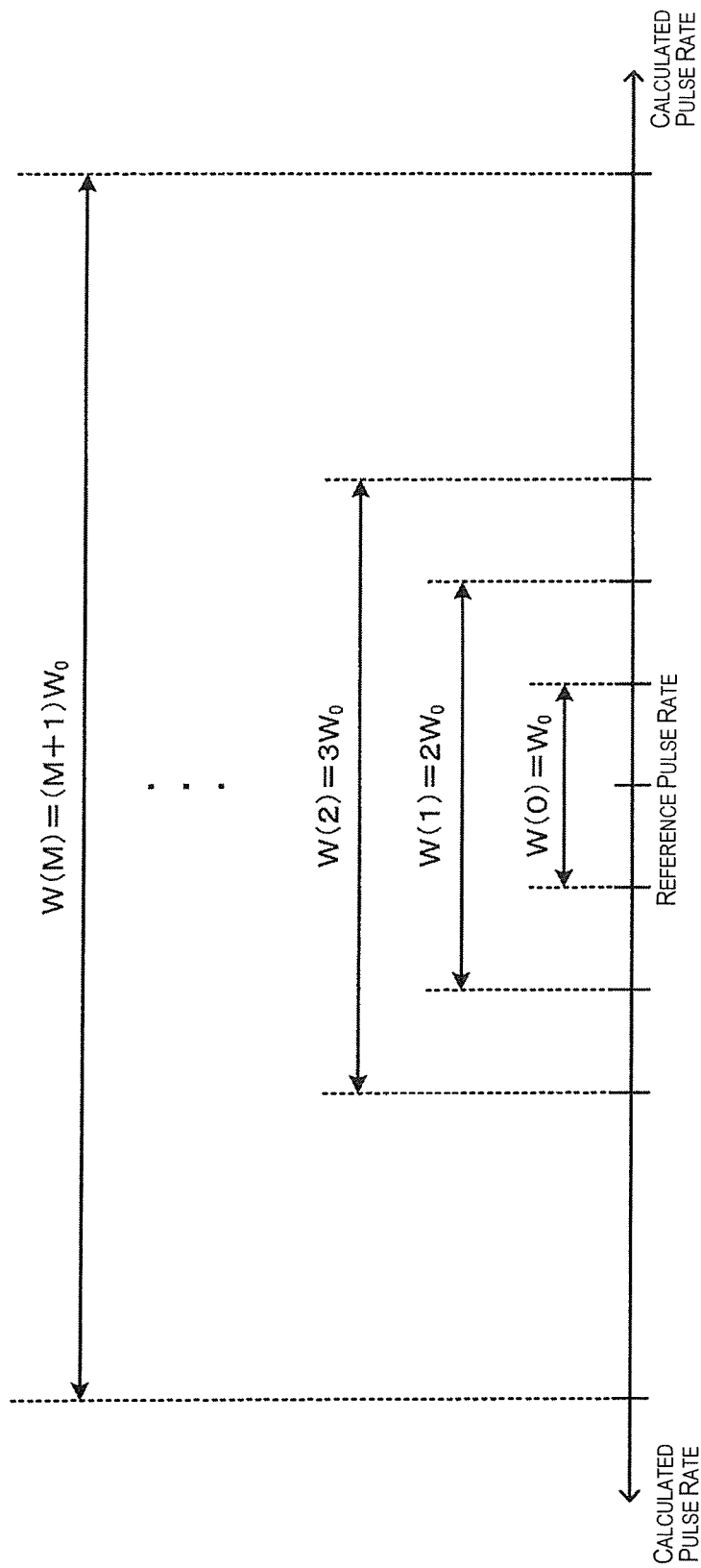
FIG. 11 shows the first setting method of window width according to the second embodiment of the invention.

FIG. 11 illustrates the first setting method of the window width. In FIG. 11, the horizontal axis is an axis of the pulse rate and its center is the reference pulse rate. When a certain calculation timing is focused, it illustrates the horizontal axis having a range that the calculated pulse rate is obtainable and the reference pulse rate is located as its center.

In the first setting method, the window "W" is linearly increasing in accordance with the value of the number of times "N" that improperness is consecutively judged. In detail, for example, the window "W(N)" is defined in accordance with the following formula (1).

$$W(N) = W_0 \cdot (N+1) \qquad [\text{formula (1)}]$$

According to the formula (1), when the number of times is N=0, the window width "$W_0$" is defined as the initial window width ($W(0)=W_0$). When the number of times is N=1, the window width "$2W_0$", which is wider than the initial window width "$W_0$", is defined ($W(1)=2W_0$). Also, when it is N=2, the window width "$3W_0$", which is wider than "$2W_0$", is defined ($W(2)=3W_0$).

Figure 12:
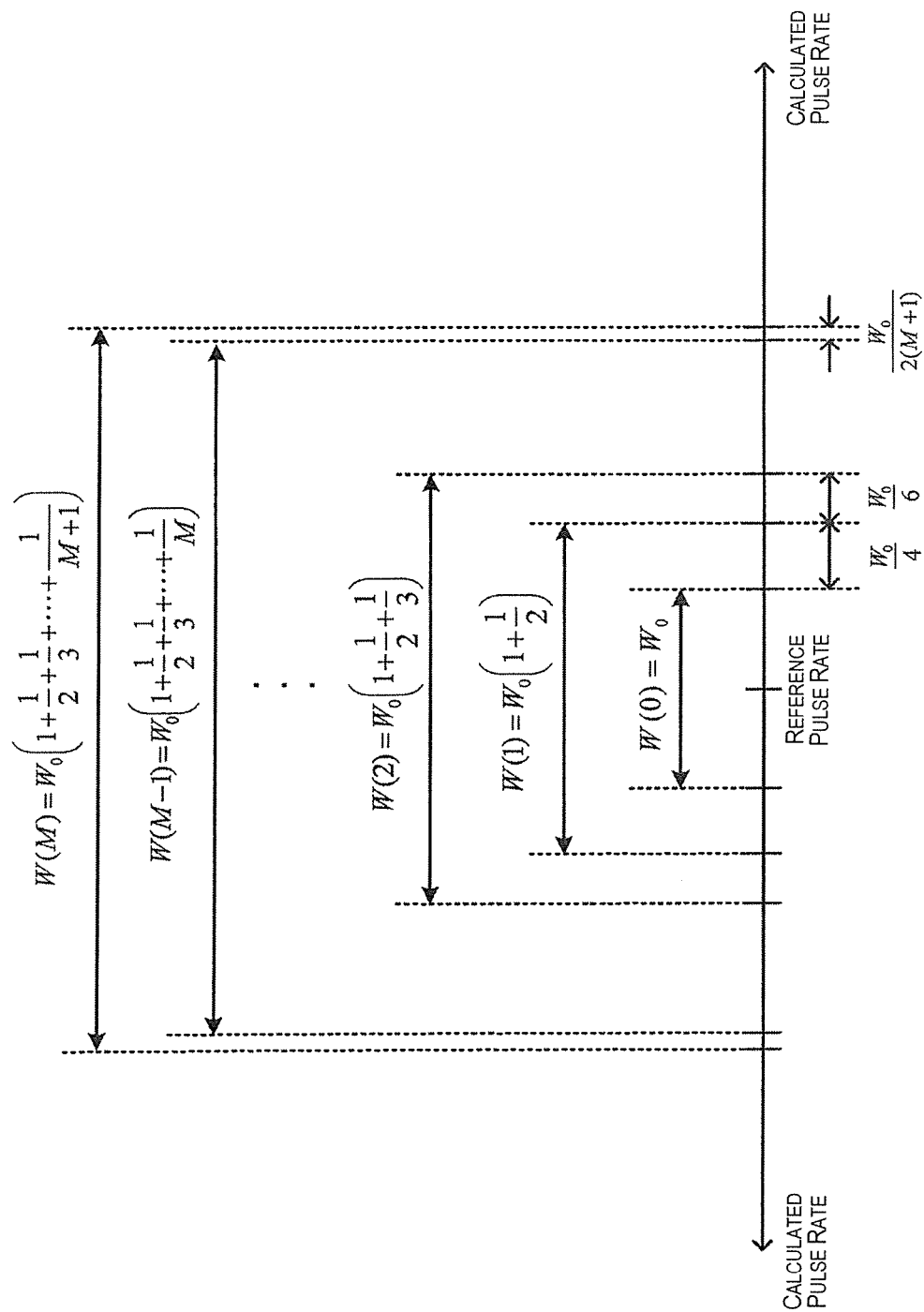
FIG. 12 shows the second setting method of window width according to the second embodiment of the invention.

FIG. 12 illustrates the second setting method of the window width. As shown in FIG. 11 illustrating the first setting method, as the value of the number of times "N" that the improperness is consecutively judged becomes larger, the window (W) linearly increases. Therefore, in a situation that the improperness is continuously judged, the window width can be stretched excessively.

Normally, there is a situation that the pulse rate of the test subject changes rapidly. Once, after the pulse rate having the rapid change, the pulse rate tends to stabilize gradually. The window is defined by the assumption of the range acquiring a variation of the pulse rate. However, it is a rare situation that the pulse rate of the test subject continuously changes by the maximum range of the window. Thus, it is effective that as the value of the number of times (N), that the improperness is consecutively judged, increases, the increase degree of the window width is reduced. In detail, for example, the window "W(N)" is defined in accordance with the following formula (2).

$$W(N) = W_0 \cdot \sum_{n=0}^{N} \frac{1}{n+1} \qquad [\text{formula (2)}]$$

According to the formula (2), when the number of times is N=0, the window width "$W_0$" is defined as the initial window width ($W(0)=W_0$). When the number of times is N=1, "$\Delta W(1)=W_0/2$" is defined as the amount of change of the window width, and the window width "$W_0(1+\frac{1}{2})$" is defined ($W(1)=W_0(1+\frac{1}{2})$). When the number of times is N=2, "$\Delta W(2)=W_0/3$" is defined as the amount of change of the window width, and the window width "$W_0(1+\frac{1}{2}+\frac{1}{3})$" is defined ($W(2)=W_0(1+\frac{1}{2}+\frac{1}{3})$). In fact, according to the formula (2), the increase degree of the window width is reduced by "$1/(N+1)$".

3-2. Functional Configuration of Second Embodiment

Figure 13:
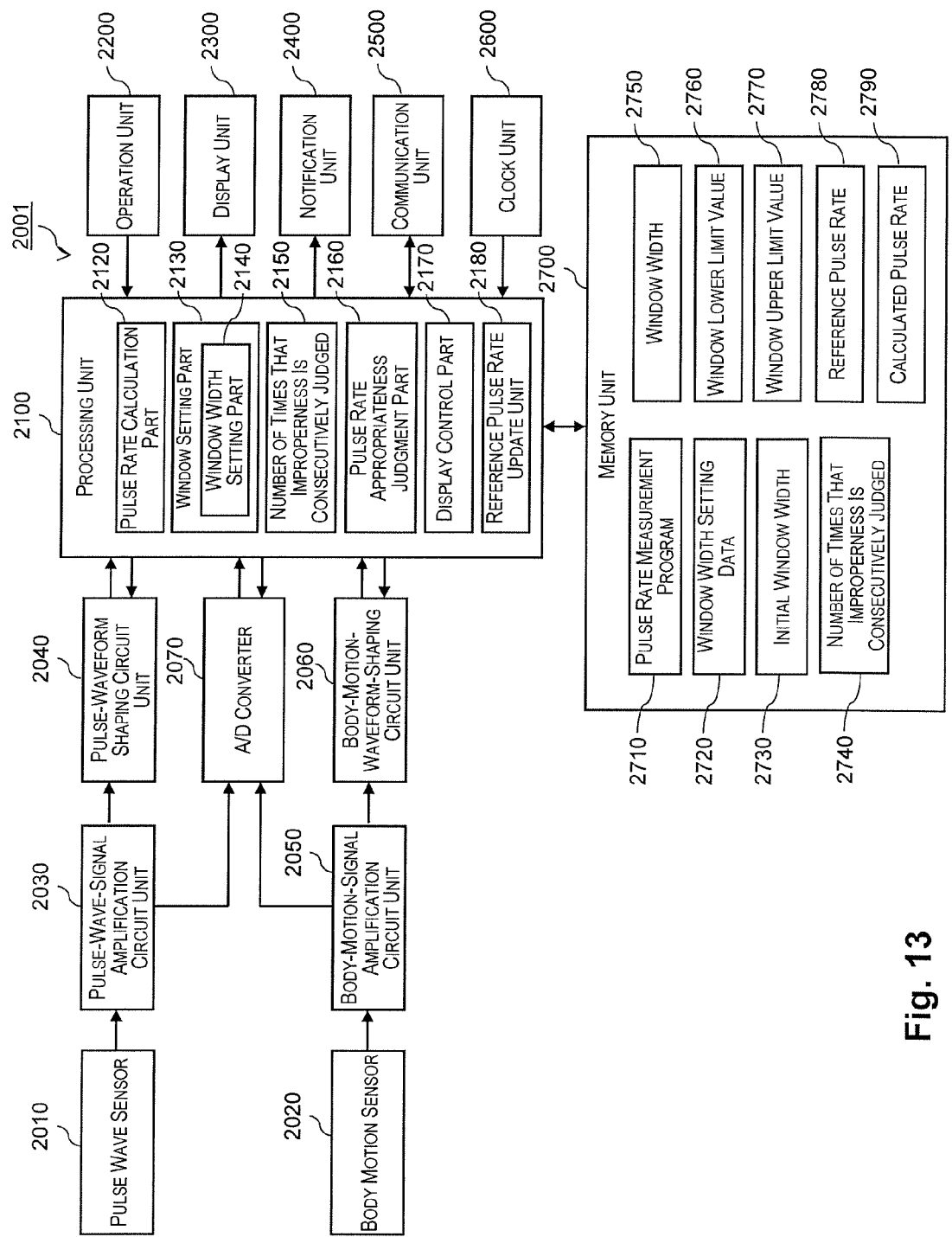
FIG. 13 is a block diagram showing a functional configuration of a pulse rate monitor according to the second embodiment of the invention.

FIG. 13 is a block diagram showing one of the examples of the functional configuration of the pulse rate monitor 2001 corresponding to the first example and the second example of the second embodiment. The pulse rate monitor 2001 includes a pulse wave sensor 2010, a body motion sensor 2020, a pulse-wave-signal amplification circuit unit 2030, a pulse-waveform shaping circuit unit 2040, a body-motion-signal amplification circuit unit 2050, a body-motion-waveform-shaping circuit unit 2060, an A/D (Analog/Digital) convertor 2070, a processing unit 2100, an operation unit 2200, a display unit 2300, a notification unit 2400, a communication unit 2500, a clock unit 2600, and a memory unit 2700.

The pulse wave sensor 2010 is a sensor to measure a pulse wave of the test subject wearing the pulse rate monitor 2001, and for example, the pulse wave sensor is configured so as to have a photoelectric pulse wave sensor. The pulse wave sensor 2010 detects, as a pulse wave signal, a change in volume generated by inflow of blood into a body tissue, and outputs the pulse wave signal to the pulse-wave-signal amplification circuit unit 2030.

The pulse-wave-signal amplification circuit unit 2030 is an amplification circuit for amplifying, by a predetermined gain, the pulse wave signal inputted from the pulse wave sensor 2010. The pulse-wave-signal amplification circuit unit 2030 outputs the amplified pulse wave signal to the pulse-waveform shaping circuit unit 2040 and the A/D converter 2070.

The pulse-waveform shaping circuit unit 2040 is a circuit unit for shaping the pulse wave signal that has been amplified by the pulse-wave-signal amplification circuit unit 2030, and is configured so as to have a circuit for removing a high-frequency noise component, a clipping circuit, and other elements. The processing unit 2100 judges, on the basis of a pulse waveform that has been shaped by the pulse-waveform shaping circuit unit 2040, whether or not a pulse wave has been detected.

The body motion sensor 2020 is a sensor for establishing the movement of the test subject wearing the pulse rate monitor 2001, and is configured so as to have at least an acceleration sensor. The body motion sensor 2020 corresponds to a body-motion-detector for detecting the body motion of the test subject.

The body-motion-signal amplification circuit unit 2050 is an amplification circuit for amplifying, by a predetermined gain, the body motion signal inputted from the body motion sensor 2020. The body-motion-signal amplification circuit unit 2050 outputs the amplified body motion signal to the body-motion-waveform-shaping circuit unit 2060 and the A/D converter 2070.

The body-motion-waveform-shaping circuit unit 2060 is a circuit unit for shaping the body motion signal that has been amplified by the body-motion-signal amplification circuit unit 2050, and is configured so as to have a circuit for removing a high-frequency noise component, a circuit for determining a gravitational acceleration component and other components, a clipping circuit, and other elements. The processing unit 2100 judges, on the basis of a body motion waveform shaped by the body-motion-waveform-shaping circuit unit 2060, whether or not body motion has been detected.

The A/D converter 2070 samples and digitizes, at predetermined sampling time intervals and, and converts to a digital signal, the pulse wave signal of the analog format amplified by the pulse-wave-signal amplification circuit unit 2030 and the body motion signal of the analog format amplified by the body-motion-signal amplification circuit unit 2050. Then, the A/D converter 2070 outputs the converted digital signal to the processing unit 2100.

The processing unit 2100 is a control device and a computation device for performing overall control of each of the units of the pulse rate monitor 2001 according to a variety of programs, such as a system program, stored in the memory unit 2700, and is configured so as to have a processor such as a central processing unit (CPU) or DSP (Digital Signal Processor). The processing unit 2100 performs a second pulse rate measurement process A according to a pulse rate measurement program 2710 stored in the memory unit 2700, and performs a control so that the pulse rate of the test subject wearing the pulse rate monitor 2001 is calculated/measured and displayed on the display unit 2300.

The processing unit 2100 includes, for example, a pulse rate calculation part 2120, a window width setting part 2130, a counting part that counts the number of times that the improperness is consecutively judged 2150, a pulse rate appropriateness judgement part 2160, a display control part 2170, and a reference pulse rate update unit 2180. However, these functional parts are one of the examples so that this is not always required by configuring all of the functional parts.

The pulse rate calculation part 2120 processes removing a body motion noise component from the pulse wave signal (pulse wave data) by using the body motion signal (body motion data) inputted from the A/D converter 2070. Then, the pulse rate calculation part 2120 calculates the pulse rate of the test subject by using the extracted pulsation components (pulsation data).

The window setting part 2130 sets a window to use an appropriateness judgment of the calculated pulse rate 2790 in the pulse rate appropriateness judgment part 2160. The window setting part 2130 has a window width setting part 2140. Then, a window lower limit value 2760 and a window upper limit value 2770 are calculated based on the window width 2750 set by the window width setting part 2140 and a latest reference pulse rate 2780.

The window width setting part 2140 sets a window width according to the above principle, by using window width setting data 2720 stored in the memory unit 2700. The window width setting part 2140 corresponds to a variation acceptable range setting part.

The counting part that counts the number of times that the improperness is consecutively judged 2150 consecutively counts the number of times (number of times that the improperness is consecutively judged) that the pulse rate appropriateness judgment part 2160 judges the calculated pulse rate 2790 being improper.

The pulse rate appropriateness judgment part 2160 judges, by using the window set by the window setting part 2130, an appropriateness of the calculated pulse rate 2790 calculated by the pulse rate calculation part 2120.

The display control part 2170 displays the pulse rate based on the results of the pulse rate appropriateness judgment part 2160 on the display unit 2300. In detail, when the pulse rate appropriateness judgment 2160 determines that the calculated pulse rate 2790 is appropriate, the calculated pulse rate 2790 is displayed as the measured pulse rate (measurement result) on the display unit 2300. On the other hand, when the pulse rate appropriateness judgment 2160 determines that the calculated pulse rate 2790 is improper, the latest reference pulse rate 2780 is displayed as the measured pulse rate (measurement result) on the display unit 2300.

When the pulse rate appropriateness judgment part 2160 determines that the calculated pulse rate 2790 is appropriate, the reference pulse rate update part 2180 updates the reference pulse rate 2780 according to the calculated pulse rate 2790.

The operation unit 2200 is configured so as to have button switches as an input device, and outputs a signal corresponding to a pressed button to the processing unit 2100. The operation unit 2200 is operated to input a variety of commands, such as a command for measuring the pulse rate. The operation unit 2200 corresponds to the operation buttons 5 shown in FIG. 1.

The display unit 2300 is a display device configured so as to have a liquid crystal display (LCD) and other elements and used for performing a variety of displays on the basis of a display signal inputted from the processing unit 2100. The display unit 2300 displays a variety of biological information (pulse rate, exercise intensity, calorie consumption, etc.). The display unit 2300 corresponds to the liquid crystal display 4 shown in FIG. 1.

The notification unit 2400 is a notification device configured so as to have a speaker, a piezoelectric vibrator, or a similar device, and used for performing a variety of notifications based on a notification signal inputted from the processing unit 2100. The notification unit 2400 performs a variety of notifications for the benefit of the test subject by, e.g., outputting an alarm sound from a speaker or causing a piezoelectric vibrator to vibrate.

The communication unit 2500 is a communication device for transmitting/receiving, in accordance with a control performed by the processing unit 2100, information used within a device, with respect to a personal computer (PC) or another external information processing device. A variety of methods can be applied as a communication method for the communication unit 2500, such as a format in which a wired connection is established through a cable that conforms to predetermined communication standards, a format in which a connection is established using an intermediate device known as a cradle that also functions as a charger, or a format in which a wireless connection is established using near field communication.

The clock unit 2600 is a time-measuring device configured so as to have a device such as a crystal oscillator including a crystal unit and an oscillation circuit, and used for measuring the time. The time measured by the clock unit 2600 is continually outputted to the processing unit 2100.

The memory unit 2700 is configured by read-only memory (ROM), flash ROM, random-access memory (RAM), or another memory device. The memory unit 2700 stores a system program of the pulse rate monitor 2001, and other programs, data for realizing a pulse rate measurement function, exercise intensity measurement function, calorie measurement function, and other functions. The memory unit 2700 also has a work area for temporarily storing mid-process data, processing results relating to a variety of processes.

3-2-1. First Example of Second Embodiment

Figure 14:
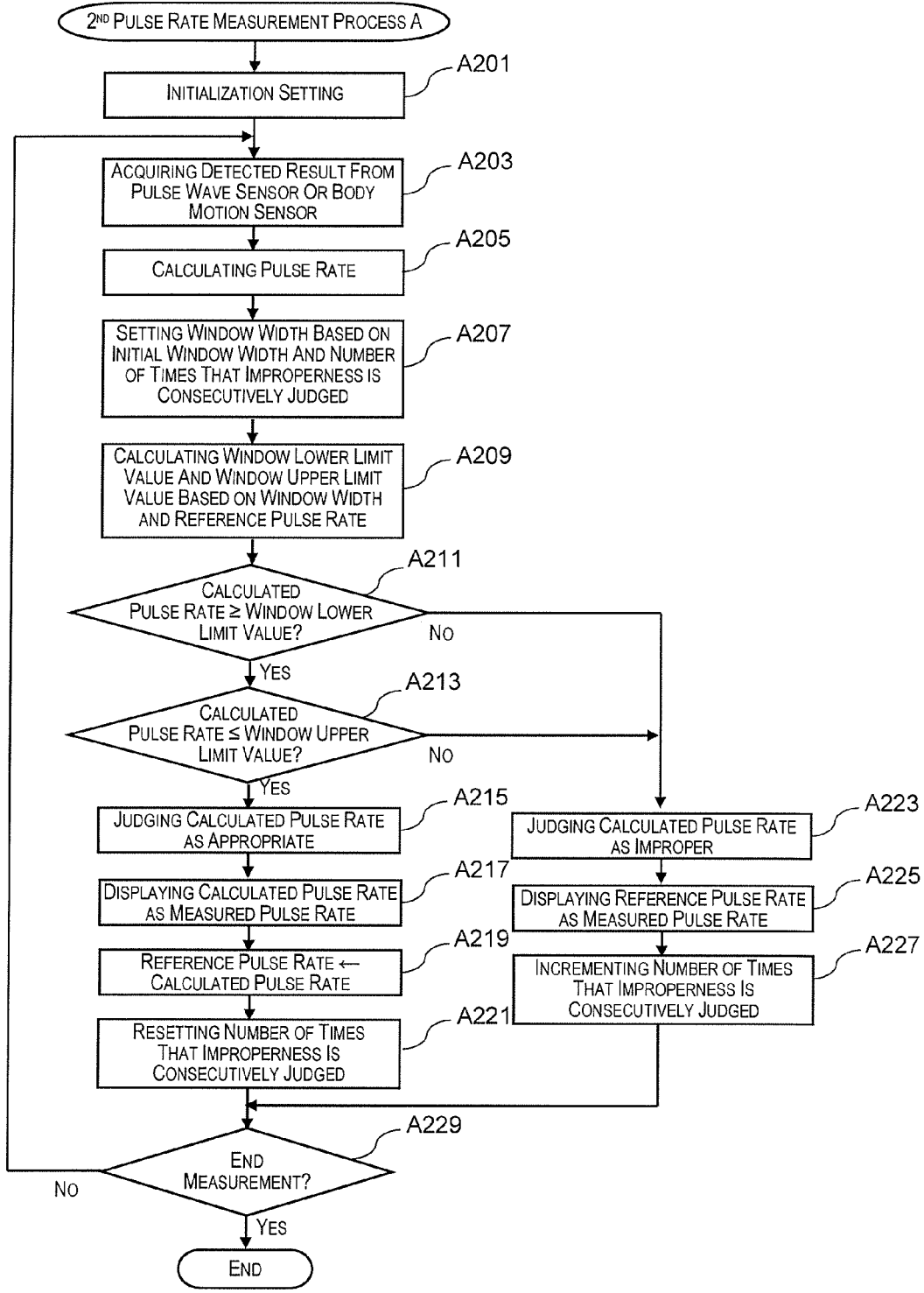
FIG. 14 is a flow chart showing the flow of the second pulse rate measurement process A according to the second embodiment of the invention.

In the first example, in the memory unit 2700 of the pulse rate monitor 2001, as a program, the pulse rate measurement program 2710 is stored for executing the second pulse rate measurement process A (shown in FIG. 14). Also, as data, the memory unit 2700 stores window width setting data 2720, an initial window width 2730, a number of times that the improperness is consecutively judged 2740, a window width 2750, a window lower limit value 2760, a window upper limit value 2770, a reference pulse rate 2780, and a calculated pulse rate.

The window width setting data 2700 is data for using the setting of the window width in the window width setting part 2140. For example, the window width setting data 2700 includes the model function of the window width as principally explained above formula (1) and formula (2), and a table that the number of times that the improperness is consecutively judged corresponds to a window width.

3-2-2. Process Flow of Second Embodiment

FIG. 14 is a flow chart showing the flow of the second pulse rate measurement process A executed in the pulse rate monitor 2001 due to the pulse rage measurement program 2710 stored in the memory unit 2700 being read by the processing unit 2100.

First, the processing unit 2100 performs initialization setting (step A201). In detail, the initial value of the number of times that the improperness is consecutively judged 2740 is set "0 time". Also, a predetermine value is set as an initial value of the reference pulse rate 2780 (e.g., rest pulse rate).

Next, the processing unit 2100 acquires the results of detection in the pulse wave sensor 2010 and the body motion sensor 2020 (step A203). Then, the pulse rate calculation part 2120 calculates the pulse rate of the test subject by using the results of the detection of pulse wave signal in the pulse wave sensor 2010 and the results of the detection in the body motion sensor 2020, and a calculated pulse rate 2790 in the memory unit 2700 is updated by using the calculated results (step A205).

After that, the window width setting part 2140 sets the window width 2750 by using the window width setting data 2720 based on the initial window width 2730 and the number of times that the improperness is consecutively judged 2740 stored in the memory unit 2700, and the window width 2750 is stored in the memory unit 2700 (step A207).

Next, the window setting part 2130 calculates the window lower limit value 2760 and the window upper limit value 2770 by using the window width 2750 and the reference pulse rate 2780 in the memory unit 2700, and the window lower limit value 2760 and the window upper limit value 2770 are stored in the memory unit 2700 (step A209).

After that, the pulse rate appropriateness judgement part 2160 judges whether or not the calculated pulse rate 2790 is more than the window lower limit value 2760 (step A211). When this condition is satisfied (step A211; Yes), the pulse rate appropriateness judgement part 2160 judges whether or not the calculated pulse rate 2790 is less than the window upper limit value 2770 (step A213). When this condition is satisfied (step A213; Yes), the pulse rate appropriateness judgement part 2160 judges that the calculated pulse rate 2790 is appropriate (step A215).

In this case, the display control part 2170 displays the calculated pulse rate 2790 as measured pulse rate on the display unit 2300. Also, the reference pulse rate update part 2180 updates the reference pulse rate 2780 by using the calculated pulse rate 2790 (step A219). In addition, the counting part that counts the number of times that the improperness is consecutively judged 2150 resets the number of times that the improperness is consecutively judged 2740 in the memory unit 2700 (step A221).

On the other hand, when the condition was not satisfied by the judgement in step A211 or step A213 (step A211; No, or step A213; No), the pulse rate appropriateness part 2160 judges that the calculated pulse rate 2790 was improper (step A223).

In this case, the display control part 2170 displays the reference pulse rate 2780 as measured pulse rate on the display unit 2300 (step A225). Also, the counting part that counts number of times that the improperness is consecutively judged 2150 increments the number of times that the improperness is consecutively judged 2740 of the memory unit 2700 by "1" (step A227).

After steps A221 or A227, the processing unit 2100 judges whether or not the pulse rate measurement is ending (step A229). For example, the processing unit 2100 judges whether or not the test subject operates that the pulse rate measurement is ending through the operation unit 2200. When the processing unit 2100 judges that the measurement is not ending (step A229; No), it returns to step 203. Also, when the processing unit 2100 judges that the measurement is ending (step A229; Yes), the second pulse rate measurement process A is completed.

3-2-3. Effect of First Example of the Second Embodiment

In the pulse rate monitor 2001, the pulse rate of the test subject is calculated by the pulse rate calculation part 2120. Also, the pulse rate appropriateness judgement part 2160 judges an appropriateness of the pulse rate based on whether or not the pulse rate calculated by the pulse rate calculation part 2120 is within the predetermined window. Then, the window width setting part 2140 sets a window width based on a value of number of times that the improperness is consecutively judged (improperness judgement) in the pulse rate appropriateness judgement part 2160.

It is possible to respond to the pulse rate changes by setting a flexible window width based on a value of the number of times that the improperness is consecutively judged, and it is not set by the fixed window width. More specifically, as a value of the number of times that the improperness is consecutively judged increases, the window width increases so that the window is able to follow the pulse rate changes.

In this case, for example, by linearly increasing the window width corresponding to the value of the number of times that the improperness is consecutively judged, the calculated pulse rate is accurately acquired in the window even if the pulse rate changes rapidly at the start of exercise or the stop of exercise.

Also, a possibility for stretching the window excessively can be avoided and a possibility for acquiring an abnormal value in the window decreases by reducing the increase degree of the window width, as the value of the number of times that the improperness is consecutively judged increases. Even if the pulse rate of the test subject changes rapidly, after that, the pulse rate tends to stabilize gradually. Therefore, it is possible to perform an appropriateness judgement by setting an appropriate window for the changes of the real human pulse rate.

Also, by narrowing a window at the initialization setting, even if an abnormal value of a calculated pulse rate is unexpectedly acquired, it is possible to exclude the abnormal value. Also, by increasing a window width corresponding to the increase of the number of times that the improperness is consecutively judged, even if the pulse rate changes rapidly, it is possible to acquire the calculated pulse rate relatively in the early stage so as to improve the responsiveness (real-time responsiveness).

3-3. Second Example of the Second Embodiment

The second example is an example that the pulse rate calculation part 2120 judges a reliability of a result of a calculated pulse rate. The window as explained in the first example and the reliability of the result of the calculated pulse rate are used to judge an appropriateness of the calculated pulse rate.

3-3-1. Configuration of Second Example of the Second Embodiment

In the second embodiment, the processing unit 2100 of FIG. 13 includes a reliability judgement part (not shown) for judging a reliability of a calculated result of the pulse rate calculation part 2120. For example, the reliability of the calculated result is judged based on a signal to noise ratio (hereafter referred to as "SN ratio") of a pulse wave signal detected by the pulse wave sensor 2010.

In this case, the pulse rate appropriateness judgement part 2160 judges that the calculated pulse rate 2790 is appropriate when the SN ratio calculated by the reliability judgement part is satisfied with a predetermined threshold value condition and, moreover, the calculated pulse rate 2790 is within a window. Otherwise, the pulse rate appropriateness judgement part 2160 judges that the calculated pulse rate 2790 is improper.

3-3-2. Process Flow of Second Example of the Second Embodiment

Figure 15:
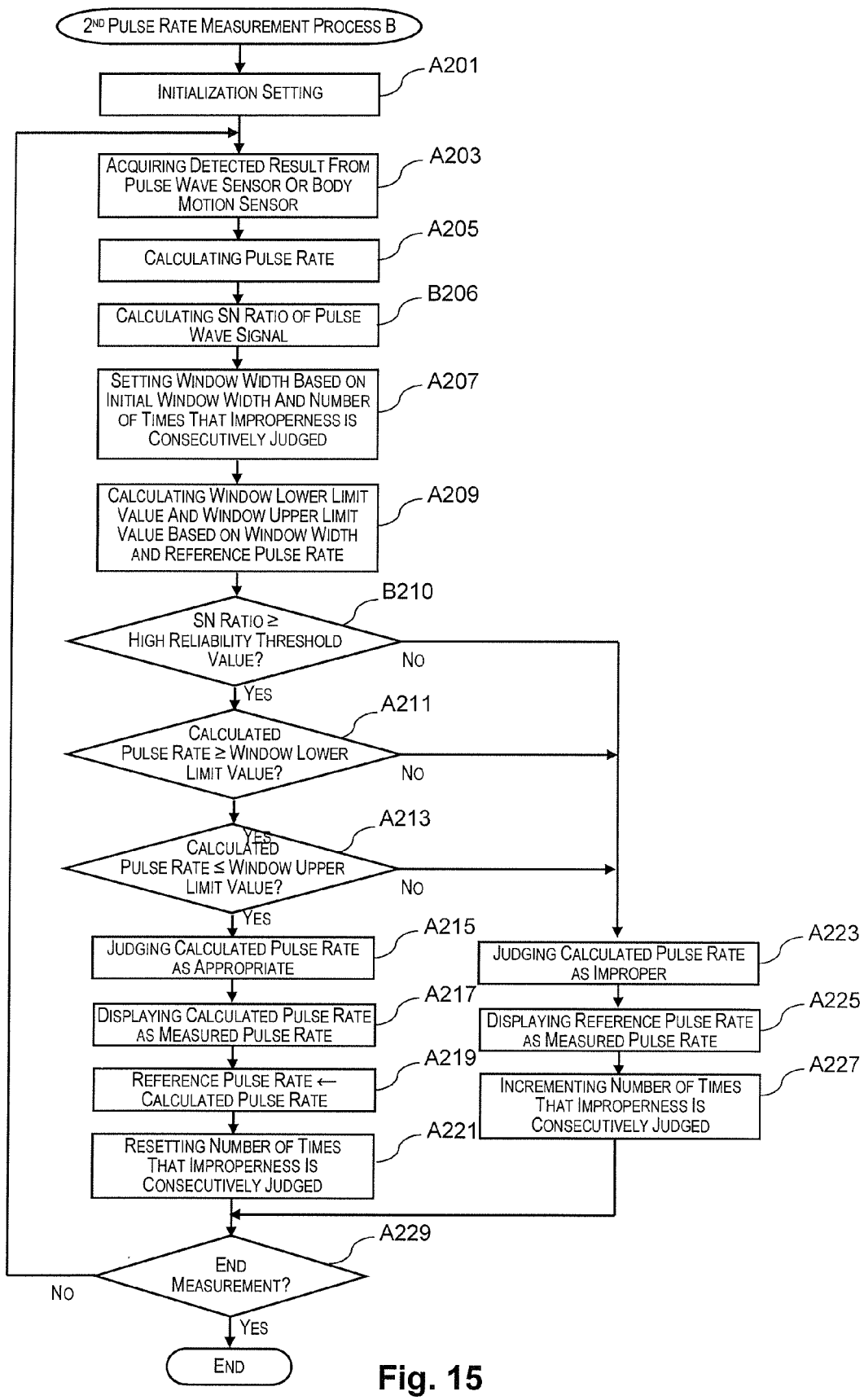
FIG. 15 is a flow chart showing the flow of the second pulse rate measurement process B.

In the second example, FIG. 15 is a flow chart showing the flow of the second pulse rate measurement process B executed, instead of the second pulse rate measurement process A of FIG. 14, in the processing unit 2100. Also, the same symbols are used to represent the same steps of the second pulse rate measurement process A, and their detailed explanations are omitted.

After calculating the pulse rate in step A205, the processing unit 2100 calculates the SN ratio of the pulse wave signal detected by the pulse wave sensor 2010 (step B206). For example, the SN ratio is calculated as follows.

The frequency analysis process is performed to the digitized pulse wave signal (pulse wave data). Then, a base line that becomes a maximum spectrum value is selected, and this becomes a pulse base line of the test subject. Also, base lines within the predetermined peripheral range of the pulse base line are excluded, and in the excluded base lines, for example, a base line having the second largest spectrum value is selected as a noise base line. The "SN ratio=$P_S/P_N$" is calculated by using the spectrum value of the pulse base line "$P_S$" and the spectrum value of the noise base line "$P_N$".

The reliability of the pulse rate calculated by the result of the frequency analysis process becomes lower because the base lines having larger spectrum are mixed so that it is difficult to distinguish between a signal component and a noise component. In this situation, the SN ratio of the pulse signal tends to be smaller. Therefore, a threshold value is defined for the SN ratio, and when the threshold value of the SN ratio is exceeded, it is judged that the reliability of the calculated result is high.

In this case, the pulse rate appropriateness judgement part 2160, after step A209, judges whether or not the SN ratio calculated in step B206 is more than the predetermined high reliability threshold value. Then, when this condition is satisfied (step B210; Yes), it assumes that reliability of the result of the calculated pulse rate is high, so as to move to the judgement using a window (steps A211, A213).

On the other hand, when it is judged that the SN ratio does not achieve the high reliability threshold value (step B210; No), the processing unit 2100 assumes that reliability of the result of the calculated pulse rate is low so as to judge that the calculated pulse rate is improper (step A223).

3-3-3. Effect of the Second Example of the Second Embodiment

In the second example, the signal to noise ratio of the pulse rate satisfies the predetermined threshold value condition, and moreover, when the calculated pulse rate is within the window, the calculated pulse rate is determined as an appropriate. Not only the window but also the reliability of the calculated result of the pulse rate is added for the reference of the judgment. Therefore, the accuracy for the appropriateness judgment of the calculated pulse rate is further improved.

3-4. Modification Example of the Second Embodiment

The modification example of the second embodiment will now be described.

3-4-1. Biological Information Processing Device

In the second embodiment, a description was given using a wristwatch-type pulse rate monitor as an example of a biological information processing device; however, a biological information processing device to which the invention can be applied is not limited to that described. For example, the invention can also be applied to a finger-worn pulse rate monitor, which is worn on the finger when the pulse rate is measured. Also, the method for detecting the pulse wave signal is not limited to a detection method in which light is used; a detection method in which ultrasound is used, or a detection method in which cardiograph is used, is also possible.

3-4-2. Body-Motion-Detector

In the second embodiment, it was described that the body motion sensor, which is the body-motion-detector, is configured so as to have an acceleration sensor. However, the body motion sensor can also be configured so as to have another sensor instead of an acceleration sensor. For example, the body motion sensor can be configured so as to have a gyro sensor, and the body motion of the test subject is detected based on the angular velocity detected by the gyro sensor. Of course, the body motion sensor can be configured so as to have both the acceleration sensor and the gyro sensor, and by using the results detected by these sensors, the body motion of the test subject can be detected.

3-4-3. Reference for Setting a Window Width

In the second embodiment, the reference for setting the window width is defined as the number of times of the consecutive improperness judgments (number of times that the improperness is consecutively judged) by the appropriateness judgment of the pulse rate. However, the reference for setting the window width is not limited to that described.

For example, the continuous time that the calculated pulse rate is determined as improper (hereafter referred to as "the continuous time of the improperness judgment") by the appropriateness judgment is measured, and the window width can be defined based on the value of the continuous time of the improperness judgment. In fact, the window width can be defined based on the reference set by the continuous time of the improperness judgment determined by the pulse rate appropriateness judgment part 2160.

Also, the frequency of the improperness judgments (hereinafter referred to as "improperness judgment frequency") that the calculated pulse rate was determined as improper by the appropriateness judgment in the predetermined past period, is measured, the value of the improperness judgment frequency can be defined as the window width. It is possible that the predetermined past period can be arbitrary defined. For example, 10 times back from the present, and the improperness judgment frequency is measured within the measurement period.

In a similar manner as the second embodiment, when these references for setting are used, as the value of the continuous time of the improperness judgment increases, or as the value of the improperness judgment frequency increases, the window width increases. In this case, the window width linearly increases in accordance with the value of the continuous time of the improperness judgment or the value of the improperness judgment frequency (e.g., formula (1)). Also, the increase degree of the window width reduces in accordance with the continuous time of the improperness judgment or the value of the improperness judgment frequency becoming larger (e.g., formula (2) or formula (3)). It is possible to apply these methods.

3-4-4. Method for Setting a Window Width

The method for setting the window width described in the second embodiment is one of the examples, and of course, it is possible to set the window width arbitrary. For example, it is possible to set the window width according to the formula (3) instead of the formula (2).

$$W(N) = W_0 \cdot \sum_{n=0}^{N} \left(\frac{1}{2}\right)^n \quad \text{[formula 3]}$$

According to the formula (3), the window width is increased and at the same time, the increase degree of the window width is reduced "½" at a time, depending on the value of the number of times that the improperness is consecutively judged. Besides, for example, it is also possible to increase the window width as a logarithm function in accordance with the value of the number of times that the improperness is consecutively judged.

3-4-5. Window

In the second embodiment, a range having the same width in higher and lower directions relative to the reference pulse rate as a reference was defined as a window. However, it is also possible to define a range having a different width in higher and lower directions relative to the reference pulse rate. In fact, it is possible to have the different widths in an upper direction of the window width for acquiring a high pulse rate which is higher than the reference pulse rate, and in a lower direction of the window width for acquiring a low pulse rate which is lower than the reference pulse rate. However, again, the fact remains that it sets the window width in the respective upper and lower directions based on at least one of the number of times that the improperness is consecutively judged, the continuous time of the appropriateness judgment, and the value of the improperness judgment frequency.

3-4-6. Reliability Judgment of a Calculation Result of Pulse Rate

In the second example of the second embodiment, it describes that the reliability of the calculation result of the pulse rate is determined based on the SN ratio (signal to noise ratio) of the pulse wave signal detected by the pulse wave sensor 10. However, the SN ratio to determine the reliability is just one of the scales so that it is possible to determine the reliability based on other scales.

For example, the reliability of the calculation result is determined based on the intensity of the pulse signal (signal intensity). In detail, when the amplitude of the pulse rate is extremely small, a possibility for not acquiring the pulse rate of the test subject increases so that the reliability of the calculated pulse rate is determined as low. Also, when the pulse wave signal is suddenly scaled out, a possibility for mixing the noise increases so that the reliability of the calculated pulse rate is determined as low. Of course, it is possible to determine the reliability of the calculation result by using both the signal to noise ratio of the pulse signal and the signal intensity.

3-4-7. Reference Pulse Rate

In the second embodiment, it describes that the latest calculated pulse rate, which is determined as an appropriate in the appropriateness judgment, is set as the reference pulse rate. In detail, at the time when the calculated pulse rate is determined as an appropriate, process of updating the reference pulse rate based on the calculated pulse rate is repeated per every calculation time.

However, the pulse rate, which is possible to be set as a reference pulse rate, is not limited to that described. For example, an average value or a central value of the calculated pulse rate, which was determined as an appropriate in a period from the current calculation timing to the predetermined past calculation timing (e.g., 5 calculation timings in the past period), can be calculated and the result can be set as the reference pulse rate.

4. Third Embodiment

In the third embodiment, the pulse rate monitor 1 is indicated by the reference numeral "3001", thereby addressing each block with 3000th number. For example, the pulse wave sensor 10 is indicated by the reference numeral 3010.

4-1. Principle of the Third Embodiment

The pulse rate monitor 3001 calculates the pulse rate of the test subject by using the pulse rate signal detected by the pulse rate sensor 3010. In detail, the signal intensity value (spectrum value) per frequency range is extracted upon performing a predetermined frequency analysis process to the pulse signal. For example, a Fast Fourier Transformation (FFT) can be used to apply for the frequency analysis process. Then, the frequency spectrum corresponding to the pulse wave of the test subject extracted from the signal intensity value is identified, and the pulse rate is calculated based on that frequency (or cycle). The pulse rate monitor 3001 calculates the pulse rate in a fixed time interval (for example, 1~5 sec). In the present embodiment, the pulse rate of the test subject calculated by above is indicated as a "calculated pulse rate."

The pulse rate monitor 3001 notifies the calculated pulse rate, as the results of measurement (measured pulse rate), to the test subject by displaying on the display unit 3300. However, there is a case that the measurement result of the calculated pulse rate, which is largely deviated from the real pulse rate of the test subject, is acquired, and this happens because of a disturbance effect such as changing outside temperature or a physical effect such as shifting a position of the pulse rate monitor device 3001. In this case, the acquired pulse rate is an abnormal value, and it is not appropriate to notify this value to the test subject. Thus, an adequacy of the calculated pulse rate is judged according to the following steps in this embodiment.

In this embodiment, a window having the predetermined reference pulse rate as a reference is defined. The reference pulse rate is a reference value of the pulse rate at the time of pulse rate calculation (calculation timing). In this embodiment, the latest calculated pulse rate determined as an appropriate by the appropriateness judgment is set as the reference pulse rate. Specifically, at the time when the calculated pulse rate is determined as an appropriate, process of updating the reference pulse rate based on the calculated pulse rate is repeated at every calculation event.

In the respective calculation events, it determines whether or not the calculated pulse rate is within the window. Then, when the calculated pulse rate is within the window, the calculated pulse rate is determined as an appropriate. On the other hand, when the calculated pulse rate is not within the window, the calculated pulse rate is determined as an improper. The window is a range, which allows the variation of the calculated pulse rate (hereinafter referred to as "variation acceptable range") calculated on the basis of the predetermined reference pulse rate.

The window width having a pulse rate, which is in an upper direction relative to the reference pulse rate, is called "window width in an upper direction". Also, the window width having a pulse rate, which is in a lower direction relative to the reference pulse rate, is called "window width in a lower direction". A pulse rate, which added the window width in an upper direction to the reference pulse rate, is called "window upper limit value", which means the upper limit value of the window. Also, a pulse rate, which added the window width in a lower direction to the reference pulse rate, is called "window lower limit value", which means the lower limit value of the window. The window is defined as a range from the window upper limit value to the window lower limit value.

In the feature of the present embodiment, the window width is set based on the reference pulse rate. When the reference pulse rate is low, the pulse rate becomes difficult to go down and it tends to go up. On the other hand, when the reference pulse rate is high, the pulse rate becomes difficult to go up and it tends to go down. These features of the pulse rate are focused so that as the reference pulse rate becomes lower, the window width in an upper direction increases, and the window width in a lower direction reduces. Also, as the reference pulse rate becomes higher, the window width in a lower direction increases, and the window width in an upper direction reduces.

4-1-1. Basic for Setting a Window Width

Figure 16A:
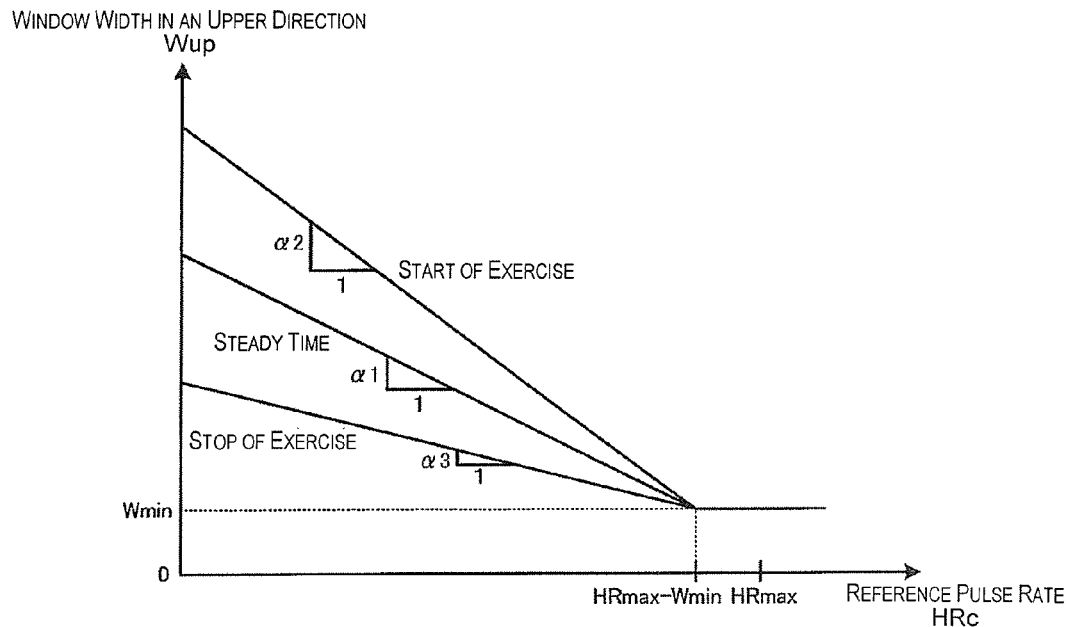
FIG. 16A shows a window width model in an upper direction according to the third embodiment of the invention.
Figure 16B:
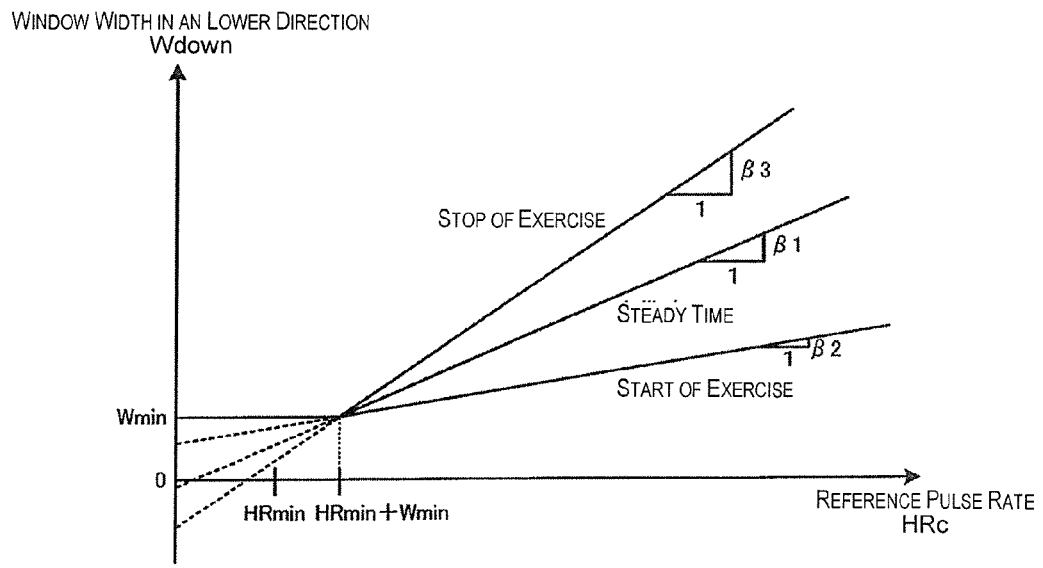
FIG. 16B shows a window width model in a lower direction according to the third embodiment of the invention.

FIG. 16 illustrates the basic method for setting a window in the present embodiment. FIG. 16A illustrates the method for setting a window width in an upper direction, and illustrates a window width model in an upper direction which is a model for setting the window width in an upper direction. FIG. 16B illustrates the method for setting a window width in a lower direction, and illustrates a window width model in a lower direction which is a model for setting the window width in a lower direction.

In FIG. 16A, the horizontal axis is the reference pulse rate "HRc", the longitudinal axis is the window width in an upper direction (Wup). Also, in FIG. 16B, the horizontal axis is the reference pulse rate "HRc", and the longitudinal axis is the window width in a lower direction (Wdown).

As shown in FIG. 16A, for example, the window width model in an upper direction has a functional model, that is the window width in an upper direction linearly reduces as the reference pulse rate "HRc" increases. In fact, the window width "Wup" has a maximum value at the reference pulse rate "HRc=0", and the linear function approximates that the window width in an upper direction "Wup" linearly reduces according to the increase of the reference pulse rate "HRc".

However, when the predetermined minimum window width "Wmin" is added to the reference pulse rate "HRc", and the acquired pulse rate is more than the maximum pulse rate "HRmax" of the test subject, the window width in an upper direction "Wup" is defined as the minimum window width "Wmin". In fact, when the reference pulse rate "HRc" is more than the predetermined pulse rate upper limit set value "HRmax−Wmin", the window width in an upper direction is defined as the predetermined minimum window width (Wup=Wmin).

The maximum pulse rate "HRmax" is the maximum pulse rate of the test subject, and for example, it is calculated by the formula (4).

[formula (4)]

$$HRmax = 220 - \text{age of the test subject} \qquad (4)$$

The minimum window width "Wmin" is the minimum value of the window width in an upper direction "Wup", and it is possible to set a selected appropriate value in advance. For example, as a value "less than 5", it can be set as the values "3" or "5".

As shown in FIG. 16B, for example, the window width in a lower direction "Wdown" has a functional model (linear function), that is the window width in a lower direction linearly increases as the reference pulse rate "HRc" increases.

However, when the minimum window width "Wmin" is reduced from the reference pulse rate "HRc", and the calculated pulse rate does not achieve the minimum pulse rate "HRmin" of the test subject, the window width in a lower direction "Wdown" is defined as the minimum window width "Wmin". In fact, when the reference pulse rate "HRc" is less than the predetermined pulse rate lower limit set value "HRmin+Wmin", the window width in a lower direction is defined as the predetermined minimum window width "Wmin" (Wdown=Wmin).

The minimum pulse rate "HRmin" is the minimum pulse rate of the test subject. It is known that the average pulse rate of the general adult person in a rest state is approximately "60~70". Therefore, for example, it can be possible to define the minimum pulse rate "HRmin" from the selected value in this range.

4-1-2. Increase Degree of a Window Width

In the present embodiment, the increase degree of the window width in an upper direction increases in comparison with the increase degree of the window width in a lower direction. At the time that the pulse rate goes up, the degree of the change tends to be increased in comparison with at the time that the pulse rate goes down. In fact, the feature that the human pulse rate tends to go up rather than going down, is focused, so that the window width is set by changing an increase degree in an upper direction and a lower direction.

In FIG. 16A, in a steady time, the angle of the window width model in an upper direction is defined as "$\alpha$". Also, in FIG. 16B, in a steady time, the angle of the window width model in a lower direction is defined as "$\beta$". In this case, the window width model in an upper direction and the window width model in a lower direction are defined as "$\alpha > \beta$". Thus, it can be possible to set wider range in the window width in an upper direction in comparison with the window width in a lower direction.

4-1-3. Setting for a Window Width Considered with the Exercise State

In the present embodiment, in addition to the above mentioned method for setting the window width, the window width is set by considering the exercise state of the test subject. The "exercise state" means the exercise state of the test subject which is determined by the changes in body movement state over time. For example, it includes "start of exercise", "during exercise", and "stop of exercise".

Also, the "body movement state" means a body movement state of the test subject detected by the detection result of the body motion sensor 3020. For example, the body movement state includes "steady state" and "exercise state". In fact, the body movement state of the test subject is determined by the detection result of the body motion sensor 3020, and the exercise state of the test subject is determined based on the changes in body movement state over time.

FIG. 16 illustrates a setting model of a window width at the start of exercise, the steady time, and the stop of exercise, individually. In FIG. 16A, an angle of a model at the steady time, a model at the start of exercise, and a model at the stop of exercise are illustrated as "$\alpha 1$", "$\alpha 2$", and "$\alpha 3$", respectively. In FIG. 16B, an angle of a model at the steady time, a model at the start of exercise, and a model at the stop of exercise are illustrated as "$\beta 1$", "$\beta 2$", and "$\beta 3$", respectively.

At the time of the start of exercise, the pulse rate of the test subject tends to go up rapidly. With that, the increase degree of the window width in an upper direction when the exercise state of the determination result is the start of exercise increases in comparison with the increase degree of the window width in an upper direction at the steady time. Also, at the time of the stop of exercise, it is rare situation that the pulse rate of the test subject goes up. With that, the increase degree of the window width in an upper direction when the determination result of the exercise state is the stop of exercise reduces in comparison with the increase degree of the window width in an upper direction at the steady time. In this case, the large and small relationship of the angle of the window width model in an upper direction in FIG. 16A is defined as "$\alpha 3 < \alpha 1 < \alpha 2$". However, in this case, the large and small relationship is defined by the absolute value of the angle.

At the time of the stop of exercise, the pulse rate of the test subject tends to go down rapidly. With that, the increase degree of the window width in a lower direction when the exercise state of the determination result is the stop of exercise increases in comparison with the increase degree of the window width in a lower direction at the steady time. Also, at the time of the start of exercise, it is rare situation that the pulse rate of the test subject goes down. With that, the increase degree of the window width in a lower direction when the determination result of the exercise state is the start of exercise reduces in comparison with the increase degree of the window width in a lower direction at the steady time. In this case, the large and small relationship of the angle of the window width model in a lower direction in FIG. 16B is defined as "$\beta 2 < \beta 1 < \beta 3$".

4-1-4. Concrete Example

FIG. 17 illustrates a concrete example. In reference to the tendency of the changes in real pulse rate over time, the method for setting the window width in the present embodiment is explained. In FIG. 17, the horizontal axis is a time axis, and the time "t" of the calculated pulse rate is shown below the time axis. Also, the longitudinal axis is the pulse rate. The calculated pulse rate is shown as a triangle plot, and the reference pulse rate is shown as a rectangular plot.

An arrow in an upper direction is provided on an upper side and an arrow in a lower direction is provided on a lower side relative to the reference pulse rate. The upper limit is set by the predetermined range in an upper direction side, and the lower limit is set by the predetermined range in a lower direction side, respectively. The window width is the difference between the upper limit value, that the arrow in the upper direction indicates the upper side relative to the reference pulse rate, and the lower limit value, that the arrow in the lower direction indicates the lower side relative to the reference pulse rate. The range defined by the window width is the variation acceptable range. Also, the window set by applying the steady time model is shown as a thin solid line, and the windows set by applying the model at the start of exercise/the model at the stop of exercise are shown as a thick solid line.

(1) At the Time of the Start of Exercise

FIG. 17A describes a method for setting a window width at the start of exercise.

The time t0 is before the start of exercise. The calculated pulse rate is slightly higher value than the minimum pulse rate "HRmin" and the value is within the window. In this case, at the time t1, the window is set by the calculated pulse rate as a reference pulse rate. More specifically, since the reference pulse rate is a lower state and the window width in an upper direction is wider, the narrow window is set for the window width in a lower direction.

After that, the test subject starts exercise between the time t1 and the time t2, and the pulse rate of the test subject goes up rapidly. In this case, the determination result of the exercise state of the test subject is the start of exercise, the window width is set by applying the model at the start of exercise. In this case, it is effective to apply the model at the start of exercise with having a certain time range. For example, 3 periods of time from the times t2~t4 are the applied periods of the model at the start of exercise. Then, in the applied periods of the model at the start of exercise, the window width is set by applying the model at the start of exercise.

As a result of the applied model at the start of exercise, at the time t2, the window width in an upper direction is set wider in comparison with the time t1. Also, the window width in a lower direction is set narrower in comparison with the time t1. At the times t3 and t4, the pulse rate of the test subject goes up and the reference pulse rate increases accordingly so that the window width in an upper direction is gradually narrowed, and the window width in a lower direction is gradually stretched. As a result, at the times t2~t4, the window follows the rapid rise of the pulse rate, and the calculated pulse rate is appropriately acquired.

After that, the application of the model at the start of exercise is released at the time t5. Specifically, at the time t5, the model at the steady time is applied to set the window width. At the time t5, the pulse rate of the test subject has been already reached high state. Since the reference pulse rate is the high state, the window width in a lower direction is set as a wide window, and the window width in an upper direction is set as a narrow window.

After that, at the time t8, it illustrates that the reference pulse rate is more than the pulse rate upper limit value "HRmax−Wmin". As a result, at the time t8, the minimum window width "Wmin" is set as a window width in an upper direction. At the times t9 and t10, it is set as a similar manner. Finally, the window width in a lower direction becomes the maximum window width, and the window width in an upper direction becomes the minimum window width.

(2) Cool-Down→at the Time of a Restart of Exercise

FIG. 17B illustrates a method for setting the window width at the time of a cool-down→at the time of the restart of exercise. In this case, it shows a situation that after the test subject performing exercise, the test subject takes a cool-down such as stretch or slow walking, and then, the test subject restarts exercise. It assumes the situation that the test subject restarts exercise from a state that the pulse rate is slightly high.

The test subject takes a cool-down period during the times t51~t56. Since the test subject performed exercise before the cool-down period, the pulse rate of the test subject maintains the slightly high during the cool-down period. After that, it illustrates that the test subject restarts exercise during the times t56~t57. At the time t56, the pulse rate has been already reached at the slightly high state. At the time t57, the window is set based on the pulse rate as a reference pulse rate. More specifically, since the reference pulse rate is slightly high state, the window width in a lower direction is set as a wide window and the window width in an upper direction is set as a narrow window.

After that, the pulse rate of the test subject goes up gradually. At the time t58, it shows a situation that an abnormal value is acquired in an upper direction as the calculated pulse rate. However, at the time t58, the window width in an upper direction is set as a narrow window. Therefore, the abnormal value is not acquired by the window, and the calculated pulse rate is determined as improper. Specifically, the window width is set based on the reference pulse rate so as to avoid the erroneous judgment such that the abnormal value is determined as a correct value.

(3) At the Time of the Stop of Exercise

FIG. 17C illustrates a method for setting the window width at the time of the stop of exercise.

The time t89 shows during exercise, and the calculated pulse rate is the maximum pulse rate "HRmax". At the time t90, the window is set based on the calculated pulse rate as a reference pulse rate. Specifically, since the reference pulse rate is high state, the window in a lower direction is set as a wide window and the window in an upper direction is set as a narrow window.

After that, it shows the stop of exercise during the times t90 and t91. In this case, since the determination result of the exercise state is the stop of exercise, the window width is set by applying the model at the stop of exercise. Also, in this case, it is effective to apply the model at the stop of exercise with having a certain time range. For example, 3 periods of time from the times t91~t93 are the applied periods of the model at the stop of exercise. Then, in the applied periods of the model the stop of exercise, the window width is set by applying the model at the stop of exercise.

As a result of the applied model at the stop of exercise, at the time t91, the window width in a lower direction is set wider in comparison with the time t90. Also, the window width in an upper direction is set narrower in comparison with the time t90. At the times t91~t93, the window follows the rapid down of the pulse rate, and the calculated pulse rate is appropriately acquired.

After that, the application of the model at the stop of exercise is released at the time t94. Specifically, at the time t94, the model at the time of the steady time is applied to set the window width. The pulse rate of the test subject is gradually reducing after passing the certain time.

After that, at the time t99, it illustrates that the reference pulse rate is less than the pulse rate lower limit value "HRmin+Wmin". As a result, at the time t99, the minimum window width "Wmin" is set as a window width in a lower direction. At the times t100, it is set in a similar manner. Finally, the window width in an upper direction becomes the maximum window width, and the window width in a lower direction becomes the minimum window width.

4-2. Functional Configuration of the Third Embodiment

Figure 18:
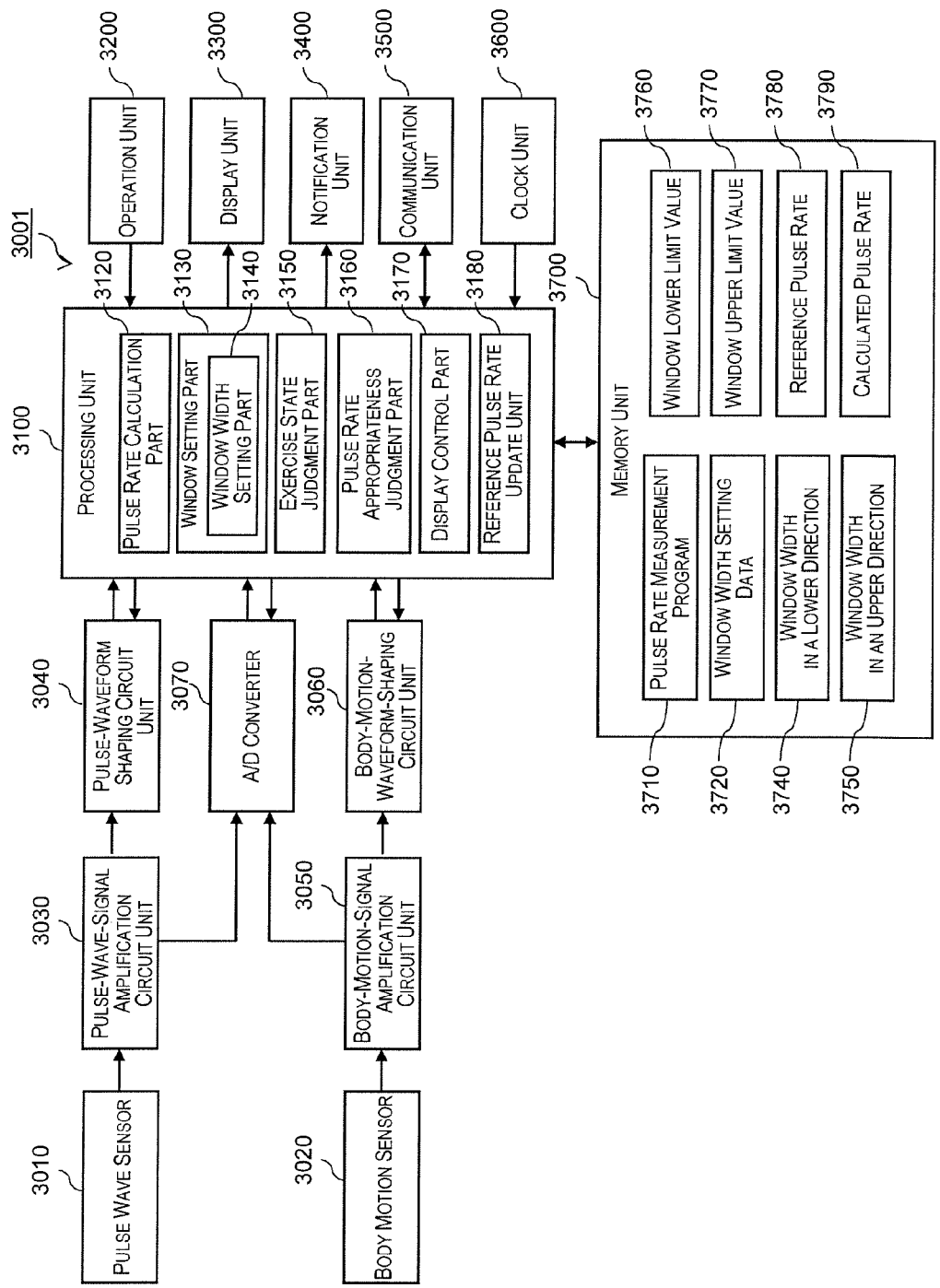
FIG. 18 is a block diagram showing a functional configuration of a pulse rate monitor according to the third embodiment of the invention.

FIG. 18 is a block diagram showing one of the examples of the functional configuration of the pulse rate monitor 3001. The pulse rate monitor 3001 includes a pulse wave sensor 3010, a body motion sensor 3020, a pulse-wave-signal amplification circuit unit 3030, a pulse-waveform shaping circuit unit 3040, a body-motion-signal amplification circuit unit 3050, a body-motion-waveform-shaping circuit unit 3060, an A/D (Analog/Digital) convertor 3070, a processing unit 3100, an operation unit 3200, a display unit 3300, a notification unit 3400, a communication unit 3500, a clock unit 3600, and a memory unit 3700.

The pulse wave sensor 3010 is a sensor to measure a pulse wave of the test subject who wears the pulse rate monitor 3001, and for example, the pulse wave sensor is configured so as to have a photoelectric pulse wave sensor. The pulse wave sensor 3010 detects, as a pulse wave signal, a change in volume generated by inflow of blood into a body tissue, and outputs the pulse wave signal to the pulse-wave-signal amplification circuit unit 3030.

The pulse-wave-signal amplification circuit unit 3030 is an amplification circuit for amplifying, by a predetermined gain, the pulse wave signal inputted from the pulse wave sensor 3010. The pulse-wave-signal amplification circuit unit 3030 outputs the amplified pulse wave signal to the pulse-waveform shaping circuit unit 3040 and the A/D converter 3070.

The pulse-waveform shaping circuit unit 3040 is a circuit unit for shaping the pulse wave signal that has been amplified by the pulse-wave-signal amplification circuit unit 3030, and is configured so as to have a circuit for removing a high-frequency noise component, a clipping circuit, and other elements. The processing unit 3100 judges, on the basis of a pulse waveform that has been shaped by the pulse-waveform shaping circuit unit 3040, whether or not a pulse wave has been detected.

The body motion sensor 3020 is a sensor for establishing the movement of the test subject wearing the pulse rate monitor 3001, and is configured so as to have, for example, an acceleration sensor. The body motion sensor 3020 corresponds to a body-motion-detector for detecting the body motion of the test subject.

The body-motion-signal amplification circuit unit 3050 is an amplification circuit for amplifying, by a predetermined gain, the body motion signal inputted from the body motion sensor 3020. The body-motion-signal amplification circuit unit 3050 outputs the amplified body motion signal to the body-motion-waveform-shaping circuit unit 3060 and the A/D converter 3070.

The body-motion-waveform-shaping circuit unit 3060 is a circuit unit for shaping the body motion signal that has been amplified by the body-motion-signal amplification circuit unit 3050, and is configured so as to have a circuit for removing a high-frequency noise component, a circuit for determining a gravitational acceleration component and other components, a clipping circuit, and other elements. The processing unit 3100 judges, on the basis of a body motion waveform shaped by the body-motion-waveform-shaping circuit unit 3060, whether or not body motion has been detected.

The A/D converter 3070 samples and digitizes, at predetermined sampling time intervals and, and converts to a digital signal, the pulse wave signal of the analog format amplified by the pulse-wave-signal amplification circuit unit 3030 and the body motion signal of the analog format amplified by the body-motion-signal amplification circuit unit 3050. Then, the A/D converter 3070 outputs the converted digital signal to the processing unit 3100.

The processing unit 3100 is a control device and a computation device for performing overall control of each of the units of the pulse rate monitor 3001 according to a variety of programs, such as a system program, stored in the memory unit 3700, and is configured so as to have a processor such as a central processing unit (CPU). The processing unit 3100 performs a third pulse rate measurement process according to a pulse rate measurement program 3710 stored in the memory unit 3700, and performs a control so that the pulse rate of the test subject wearing the pulse rate monitor 3001 is calculated/measured and displayed on the display unit 3300.

The processing unit 3100 includes, for example, a pulse rate calculation part 3120, a window width setting part 3130, an exercise state judgment part 3150, a pulse rate appropriateness judgement part 3160, a display control part 3170, and a reference pulse rate update unit 3180. However, these functional parts are one of the examples so that this does not always require configuring all of the functional parts.

The pulse rate calculation part 3120 processes removing a body motion noise component from the pulse wave signal (pulse wave data) by using the body motion signal (body motion data) inputted from the A/D converter 3070. Then, the pulse rate calculation part 3120 calculates the pulse rate of the test subject by using the extracted pulsation components (pulsation data).

The window setting part 3130 sets a window to use an appropriateness judgment of the calculated pulse rate 3790 in the pulse rate appropriateness judgment part 3160. In detail, a window lower limit value 3760 and a window upper limit value 3770 are calculated based on a window width in a lower direction 3740 and a window width in an upper direction 3750 set by the window width setting part 3140 and a latest reference pulse rate 3780.

The window width setting part 3140 sets the window width in a lower direction 3740 and the window width in an upper direction 3750 according to the above principle, by using window width setting data 3720 stored in the memory unit 3700.

The exercise state judgment part 3150 judges the exercise state (start of exercise, during exercise, stop of exercise, etc.) of the test subject based on the time changes within the predetermined time of the body motion signal (body motion data) inputted from A/D converter 3070.

The pulse rate appropriateness judgment part 3160 judges, by using the window set by the window setting part 3130, an appropriateness of the calculated pulse rate 3790 calculated by the pulse rate calculation part 3120.

The display control part 3170 displays the pulse rate based on the results of the pulse rate appropriateness judgment part 3160 on the display unit 3300. In detail, when the pulse rate appropriateness judgment 3160 determines that the calculated pulse rate 3790 is appropriate, the calculated pulse rate 3790 is displayed as the measured pulse rate (measurement result) on the display unit 3300. On the other hand, when the pulse rate appropriateness judgment 3160 determines that the calculated pulse rate 3790 is improper, the latest reference pulse rate 3780 is displayed as the measured pulse rate (measurement result) on the display unit 3300.

When the pulse rate appropriateness judgment part 3160 determines that the calculated pulse rate 3790 is appropriate, the reference pulse rate update part 3180 updates the reference pulse rate 3780 according to the calculated pulse rate 3790.

The operation unit 3200 is configured so as to have button switches as an input device, and outputs a signal corresponding to a pressed button to the processing unit 3100. The operation unit 3200 is operated to input a variety of commands, such as a command for measuring the pulse rate. The operation unit 3200 corresponds to the operation buttons 5 shown in FIG. 1.

The display unit 3300 is a display device configured so as to have a liquid crystal display (LCD) and other elements and used for performing a variety of displays on the basis of a display signal inputted from the processing unit 3100. The display unit 3300 displays a variety of biological information (pulse rate, exercise intensity, calorie consumption, etc.). The display unit 3300 corresponds to the liquid crystal display 4 shown in FIG. 1.

The notification unit 3400 is a notification device configured so as to have a speaker, a piezoelectric vibrator, or a similar device, and used for performing a variety of notifications based on a notification signal inputted from the processing unit 3100. The notification unit 3400 performs a variety of notifications for the benefit of the test subject by, e.g., outputting an alarm sound from a speaker or causing a piezoelectric vibrator to vibrate.

The communication unit 3500 is a communication device for transmitting/receiving, in accordance with a control performed by the processing unit 3100, information used within a device, with respect to a personal computer (PC) or another external information processing device. A variety of methods can be applied as a communication method for the communication unit 3500, such as a format in which a wired connection is established through a cable that conforms to predetermined communication standards, a format in which a connection is established using an intermediate device known as a cradle that also functions as a charger, or a format in which a wireless connection is established using near field communication.

The clock unit 3600 is a time-measuring device configured so as to have a device such as a crystal oscillator including a crystal unit and an oscillation circuit, and used for measuring the time. The time measured by the clock unit 3600 is continually outputted to the processing unit 3100.

The memory unit 3700 is configured by read-only memory (ROM), flash ROM, random-access memory (RAM), or another memory device. The memory unit 3700 stores a system program of the pulse rate monitor 3001, and other programs, data for realizing a pulse rate measurement function, exercise intensity measurement function, calorie measurement function, and other functions. The memory unit 3700 also has a work area for temporarily storing mid-process data, processing results relating to a variety of processes.

Figure 19:
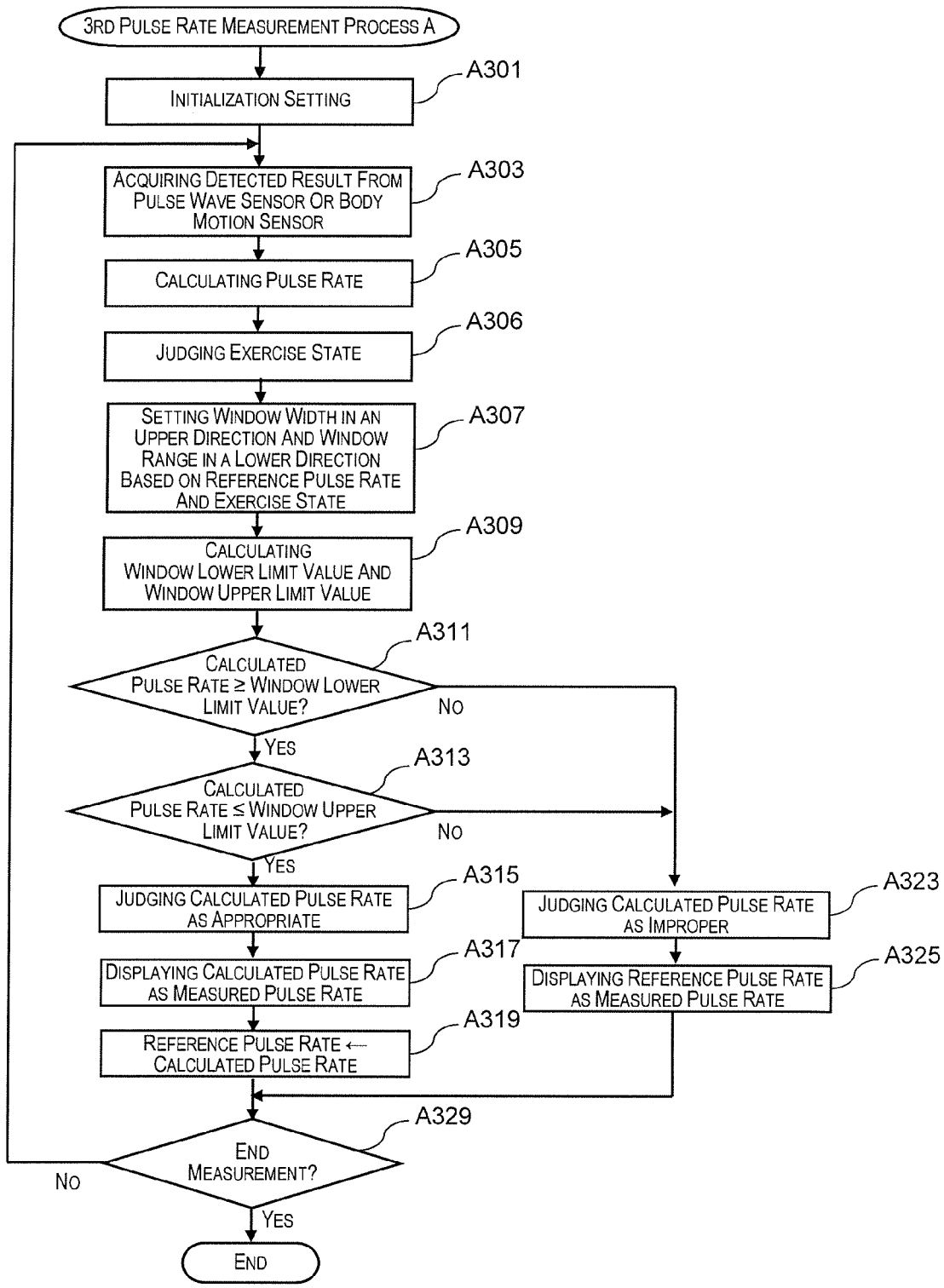
FIG. 19 is a flow chart showing the flow of the third pulse rate measurement process according to the third embodiment of the invention.

As a program, the memory unit 3700 stores a pulse rate measurement program 3710 to execute the third pulse rate measurement process (shown in FIG. 19). As data, the memory unit 3700 also stores window width setting data 3720, window width in a lower direction data 3740, window width in an upper direction data 3750, a window lower limit value 3760, a window upper limit value 3770, a reference pulse rate 3780, and a calculated pulse rate 3790.

The window width setting data 3720 is data for using the setting of a window width in the window width setting part 3140. For example, the window width setting data 3720 includes the model function data of a window width (upper limit or lower limit) and a table that a reference pulse rate corresponds to a window width (upper limit or lower limit).

4-3. Process Flow of the Third Embodiment

FIG. 19 is a flow chart showing the flow of the third pulse rate measurement process executed in the pulse rate monitor 3001 due to the pulse range measurement program 3710 stored in the memory 3700 being read by the processing unit 3100.

First, the processing unit 3100 performs initialization setting (step A301). In detail, a predetermine value (e.g., rest pulse rate) is set as an initial value of the reference pulse rate 3780.

Next, the processing unit 3100 acquires the result of detection in the pulse wave sensor 3010 and the body motion sensor 3020 (step A303). Then, the pulse rate calculation part 3120 calculates the pulse rate of the test subject by using the results of the detection of pulse wave signal in the pulse wave sensor 3010 and the results of the detection in the body motion sensor 3020, and a calculated pulse rate 3790 in the memory unit 3700 is updated by using the calculated results (step A305).

After that, the exercise state judgement part 3140 judges an exercise state based on the result of detection in the body motion sensor 3020 (step A306). Then, the window width setting part 3140 sets a window width in a lower direction 3740 and a window width in an upper direction 3750 based on the latest reference pulse rate 3780 stored in the memory unit 3700 and the exercise state judged in step A306, and the window width in a lower direction 3740 and the window width in an upper direction 3750 are stored in the memory unit 3700 (step A307).

Next, the window setting part 3130 calculates a window lower limit value 3760 and a window upper limit value 3770 by using the window width in a lower direction 3740 and the window width in an upper direction 3750 set in step A307 and the reference pulse rate 3780, and then, the window lower limit value 3760 and the window upper limit value 3770 are stored in the memory unit 3700 (step A309).

After that, the pulse rate appropriateness judgement part 3160 judges whether or not the calculated pulse rate 3790 is more than the window lower limit value 3760 (step A311). When this condition is satisfied (step A311; Yes), the pulse rate appropriateness judgement part 3160 judges whether or not the calculated pulse rate 3790 is less than the window upper limit value 3770 (step A313). When this condition is satisfied (step A313; Yes), the pulse rate appropriateness judgement part 3160 judges that the calculated pulse rate 3790 is appropriate (step A315).

Then, the display control part 3170 displays the calculated pulse rate 3790 as measured pulse rate on the display unit 3300 (step A317. Also, the reference pulse rate update part 3180 updates the reference pulse rate 3780 of the memory unit 3700 by using the calculated pulse rate 3790 (step A319).

On the other hand, when the condition was not satisfied by the judgement in step A311 or step A313 (step A311; No, or step A313; No), the pulse rate appropriateness part 3160 judges that the calculated pulse rate 3790 was improper (step A323). Then, the display control part 3170 displays the reference pulse rate 3780 as measured pulse rate on the display unit 3300 (step A325).

After steps A319 or A325, the processing unit 3100 judges whether or not the pulse rate measurement is ending (step A329). For example, the processing unit 3100 judges whether or not the test subject operates that the pulse rate measurement is ending through the operation unit 3200. When the processing unit 3100 judges that the measurement is not ending (step A329; No), it returns to step 303. Also, when the processing unit 3100 judges that the measurement is ending (step A329; Yes), the third pulse rate measurement process is completed.

4-4. Effect of the Third Embodiment

In the pulse rate monitor 3001, the pulse rate of the test subject is calculated by the pulse rate calculation part 3120. Also, the pulse rate appropriateness judgement part 3160 judges an appropriateness of the pulse rate based on whether or not the pulse rate calculated by the pulse rate calculation part 3120 is within the predetermined window. Then, the window width setting part 3140 sets a window width as a width of the window based on a predetermined reference pulse rate.

In detail, as the reference pulse rate becomes lower, the window width setting part 3140 increases the window width in an upper direction. The window width in an upper direction is the window width for the pulse rate in an upper direction relative to the reference pulse rate as a reference. In the low pulse rate state, the pulse rate becomes difficult to go down, and it tends to go up. Thus, as the reference pulse rate becomes lower, the window width in an upper direction increases.

Also, as the reference pulse rate becomes higher, the window width setting part 3140 increases the window width in a lower direction. The window width in a lower direction is the window width for the pulse rate in a lower direction relative to the reference pulse rate as a reference. In the high pulse rate state, the pulse rate becomes difficult to go up, and it tends to go down. Thus, as the reference pulse rate becomes higher, the window width in a lower direction increases.

Also, the increase degree of the pulse rate tends to increase in comparison with the down degree of the pulse rate. Then, the increase degree of the window width in an upper direction increases in comparison with the increase degree of the window width in a lower direction, so that it realizes the setting of the window width which is considered with the feature of the human pulse rate.

Also, in the present embodiment, the exercise state of the test subject is determined, and the increase degree of the window width in an upper direction when the determination result is the start of exercise increases in comparison with the increase degree of the window width in an upper direction at the time of the steady time. Also, the increase degree of the window width in a lower direction when the determination result is the stop of exercise increases in comparison with the increase degree of the window width in a lower direction at the time of the steady time. Therefore, it is possible the window to follow the rapid rise/down of the pulse rate so that the accuracy for the appropriateness judgment of the calculated pulse rate is further improved.

In the method for setting a window width in the present embodiment, the window width is set based on the reference pulse rate. Because of that, at the time of cool-down, even though the calculation starts from the state that the pulse rate is high after the exercise, or the test subject stops exercise at the time of the high pulse rate after running and the test subject starts walking, it can be possible to perform the appropriateness judgment of the calculated pulse rate by setting the appropriate window width. Specifically, when the reference pulse rate is high state, the window width in a lower direction is set as a wide window, and the window width in an upper direction is set as a narrow window. With that, even though the abnormal value is calculated in an upper direction, the window in an upper direction does not acquire the abnormal value so as to avoid the erroneous judgment such that the abnormal value is determined as a correct value.

In a similar manner, when the test subject stops movement at the time of the low pulse rate, the appropriate window width can be set to perform the appropriateness judgment of the calculated pulse rate. Specifically, when the reference pulse rate is low, the window width in an upper direction is set as a wider window, and the window width in a lower direction is set as a narrower window. Because of that, even though an abnormal value is calculated in a lower direction, the window width in a lower value does not acquire the abnormal value so as to avoid the erroneous judgment such that the abnormal value is determined as a correct value.

4-5. Modification Example of the Third Embodiment

The modification example of the third embodiment will now be described.

4-5-1. Biological Information Processing Device

In the third embodiment, a description was given using a wristwatch-type pulse rate monitor as an example of a biological information processing device; however, a biological information processing device to which the invention can be applied is not limited to that described. For example, the invention can also be applied to a finger-worn pulse rate monitor, which is worn on the finger when the pulse rate is measured. Also, the method for detecting the pulse wave signal is not limited to a detection method in which light is used; a detection method in which ultrasound is used, or a detection method in which cardiograph is used, is also possible.

4-5-2. Body-Motion-Detector

In the third embodiment, it described that the body motion sensor, which is the body-motion-detector, is configured so as to have an acceleration sensor. However, the body motion sensor can also be configured so as to have another sensor instead of an acceleration sensor. For example, the body motion sensor can be configured so as to have a gyro sensor, and the body motion of the test subject is detected based on the angular velocity detected by the gyro sensor. Of course, the body motion sensor can be configured so as to have both the acceleration sensor and the gyro sensor, and by using the results detected by these sensors, the body motion of the test subject can be detected.

4-5-3. Window Width Model

In the third embodiment, as one of the examples, it shows the model function of the window width approximated by the linear function. However, the model function of the window width, which is applicable for the invention, is not limited to that described. For example, as a model function, it can be possible to define the window width model in an upper direction, which reduces as a logarithm function in accordance with the increase of the reference pulse rate. Also, as a model function, it can be possible to define the window width model in a lower direction, which increases as a logarithm function in accordance with the increase of the reference pulse rate.

4-5-4. Method for Setting at the Time of the Start of Exercise/the Stop of Exercise In the third embodiment, at the time of the start of exercise/the stop of exercise, it described to set the period applied by the model at the start of exercise/the period applied by the model at the stop of exercise. However, for these periods, the window width models are not fixed, and it is possible to set a window width by changing an applied model.

Figure 20A:
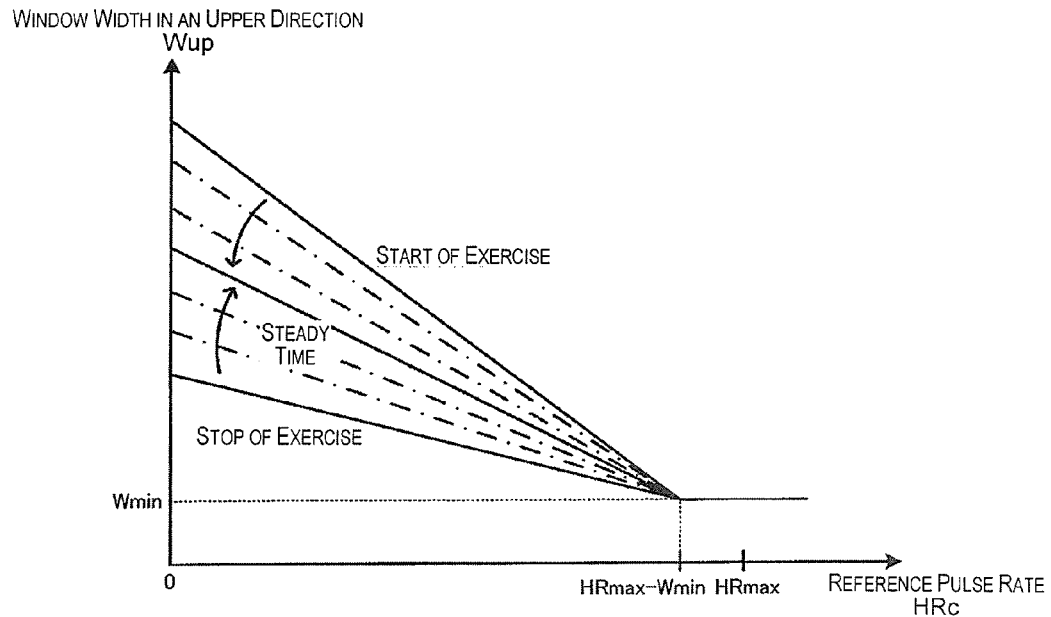
FIG. 20A shows a window width model in an upper direction according to the third embodiment of the invention.

FIG. 20 illustrates a window model in a modification example. This is similar to the way of viewing in FIG. 16. For the window width in an upper direction "Wup" shown in FIG. 20A, at the period applied by the model at the start of exercise, the model at the start of exercise gradually moves closer to the model at the steady time by reducing the angle of the model function in a step-by-step manner. Also, at the period applied by the model at the stop of exercise, the model at the stop of exercise gradually moves closer to the model at the steady time by increasing the angle of the model function in a step-by-step manner.

Figure 20B:
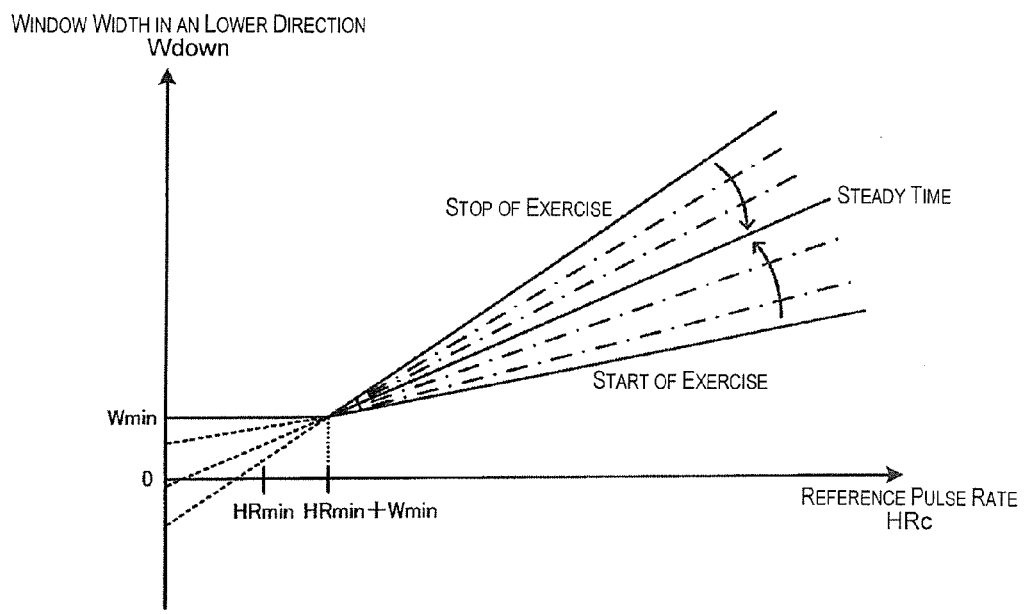
FIG. 20B shows a window width model in a lower direction according to the third embodiment of the invention.

Also, for the window width in a lower direction "Wdown" shown in FIG. 20B, at the period applied by the model at the start of exercise, the model at the start of exercise gradually moves closer to the model at the steady time by increasing the angle of the model function in a step-by-step manner. Also, at the period applied by the model at the stop of exercise, the model at the stop of exercise gradually moves closer to the model at the steady time by reducing the angle of the model function in a step-by-step manner.

4-5-5. Period Applied by the Model at the Start of Exercise/Period Applied by the Model at the Stop of Exercise In a situation that pulse rate is increasing such as at the start of exercise, the pulse rate tends to rise relatively quickly and then gradually stabilize. On the other hand, in a situation that the pulse rate is falling such as the end of exercise, the pulse rate tends to initially drop relatively insignificantly, and rapidly fall after the certain time has elapsed, and then slowly converge.

The feature of the pulse rate is focused, and the period applied by the model at the start of exercise and the period applied by the model at the stop of exercise can be set as a different length of period. As focused on the above feature of the pulse rate, it is effective that the period applied by the model at the stop of exercise is longer than the period applied by the model at the start of exercise. For example, 3 periods of time detected from the start of exercise are the period applied by the model at the start of exercise, and 6 periods of time detected from the stop of exercise are the period applied by the model at the stop of exercise.

4-5-6. Reference Pulse Rate

In the third embodiment, the reference pulse rate is set as a latest calculated pulse rate determined as an appropriate by the appropriateness judgment. Specifically, when the calculated pulse rate is determined as an appropriate, process of updating the reference pulse rate based on the calculated pulse rate is repeated per every calculation timing.

However, the pulse rate, which is possible to be set as a reference pulse rate, is not limited to that described. For example, an average value or a central value of the calculated pulse rate, which was determined as an appropriate in a period from the current calculation timing to the predetermined past calculation timing (e.g., 5 calculation timings in the past period), can be calculated and set as the reference pulse rate.

4-5-7. Maximum Pulse Rate and Minimum Pulse Rate

The methods for setting the maximum pulse rate and minimum pulse rate are not limited to that described above embodiment. For example, other than the formula (4), the test subject performs high-load exercise, the pulse rate is calculated for the predetermined time, and the maximum pulse rate "HRmax" is calculated from its average value or its central value. Also, at the rest state of the test subject, the pulse rate is calculated for the predetermined time, the minimum pulse rate "HRmin" is calculated from its average value or its central value. It is also possible to input the value of the maximum pulse rate "HRmax" or the value of the minimum pulse rate "HRmin" manually by the test subject.

What is claimed is:

1. A biological information processing device comprising:
a processor configured to
calculate a pulse rate of a test subject,
judge a deviation degree between a predetermined reference pulse rate and a calculated pulse rate,
judge, based on a reliability judgment reference, a reliability of a calculated result on the calculated pulse rate, and
judge an appropriateness of the calculated pulse rate based on the deviation degree and the reliability, the reliability judgment reference being set in accordance with the deviation degree that has been judged, the deviation degree including a first pulse range and a second pulse range each of which indicates a scale of a deviation between the predetermined reference pulse rate and the calculated pulse rate, the second pulse range being greater than the first pulse range, the reliability judgment reference including at least two predetermined reliability conditions that are different from each other, wherein the processor is further configured such that when the scale of a deviation is within the first pulse range, the processor determines that the calculated pulse rate is appropriate when a fewer number of the predetermined reliability conditions are satisfied than when the scale of a deviation is within the second pulse range.

2. The biological information processing device according to claim 1, wherein the reliability judgment reference further includes at least two reliability judgment values that are different from each other, and a reliability judgment value that the processor uses to determine the appropriateness of the calculated pulse rate when the scale of a deviation is within the first pulse range is smaller than a reliability judgment value that the processor uses to determine the appropriateness of the calculated pulse rate when the scale of a deviation is within the second pulse range.

3. The biological information processing device according to claim 2, wherein the processor is configured to judge the appropriateness of the calculated pulse rate based on the number of times affirmative judgment when the scale of the deviation is within the second pulse range.

4. The biological information processing device according to claim 2, wherein the processor is further configured to detect a body motion of the test subject, judge a frequency of a cyclic body motion of the test subject by using a detection result on the body motion that has been detected, and judge whether a predetermined frequency condition is satisfied, the predetermined frequency condition indicates that the frequency of the cyclic body motion of the test subject is away from the frequency of the calculated pulse rate, the appropriateness of the calculated pulse rate is judged by using the determination result on whether the predetermined reliability condition is satisfied and a determination result on whether the predetermined frequency condition is satisfied when the scale of the deviation is within the second pulse range.

5. The biological information processing device according to claim 2, wherein the processor is configured to detect a body motion of the test subject, judge a body movement state of the test subject by using a detection result on the body motion that has been detected, and judge whether the body movement state and the calculated pulse rate satisfy a predetermined consistency condition, and when the deviation degree satisfies a predetermined high deviation condition, the appropriateness of the calculated pulse rate is judged by using the determination result on whether the predetermined reliability condition is satisfied and a determination result on whether the body movement state and the calculated pulse rate satisfy the predetermined consistency condition.

6. The biological information processing device according to claim 5, wherein the processor is further configured to judge the appropriateness of the calculated pulse rate based on a number of times affirmative judgment being determined when the determination result on whether the predetermined reliability condition is satisfied is an affirmative judgment and further the determination result on whether the body movement state and the calculated pulse rate satisfy the predetermined consistency condition.

7. The biological information processing device according to claim 1, wherein the processor is further configured to judge the appropriateness of the calculated pulse rate based on a number of times affirmative judgment when the scale of the deviation between the reference pulse rate and the calculated pulse rate is within the second pulse range.

8. The biological information processing device according to claim 1, wherein the processor further detects a body motion of the test subject, judges a frequency of the body motion of the test subject by using a detection result on the body motion that has been detected, and judges whether the frequency of the body motion of the test subject and a frequency corresponding to the calculated pulse rate satisfy a predetermined frequency condition, and the appropriateness of the calculated pulse rate is judged by using the determination result on whether the predetermined reliability condition is satisfied and a determination result on whether the predetermined frequency condition is satisfied when the scale of the deviation between the reference pulse rate and the calculated pulse rate is within the second pulse range.

9. The biological information processing device according to claim 1, wherein the processor detects a body motion of the test subject, judges a body movement state of the test subject by using a detection result on the body motion that has been detected, and judges whether the calculated pulse rate satisfies a predetermined consistency condition that is set based on the body movement state, and when the deviation degree satisfies a predetermined high deviation condition, the appropriateness of the calculated pulse rate is judged by using the determination result on whether the predetermined reliability condition is satisfied and a determination result on whether the body movement state and the calculated pulse rate satisfy the predetermined consistency condition.

10. The biological information processing device according to claim 9, wherein the predetermined consistency condition is a threshold relating to a pulse rate that is set in according with the body movement state.

* * * * *